(12) United States Patent
Norman

(10) Patent No.: US 10,803,981 B2
(45) Date of Patent: Oct. 13, 2020

(54) APPLIED ARTIFICIAL INTELLIGENCE TECHNOLOGY FOR HORMONE THERAPY TREATMENT

(71) Applicant: James Glenn Norman, Tampa, FL (US)

(72) Inventor: James Glenn Norman, Tampa, FL (US)

(*) Notice: Subject to any disclaimer, the term of this patent is extended or adjusted under 35 U.S.C. 154(b) by 0 days.

(21) Appl. No.: 16/599,697

(22) Filed: Oct. 11, 2019

(65) Prior Publication Data

US 2020/0118662 A1  Apr. 16, 2020

Related U.S. Application Data

(63) Continuation of application No. PCT/US2019/055677, filed on Oct. 10, 2019.

(60) Provisional application No. 62/745,756, filed on Oct. 15, 2018.

(51) Int. Cl.
| | |
|---|---|
| *G16H 20/10* | (2018.01) |
| *G16H 10/60* | (2018.01) |
| *A61K 38/27* | (2006.01) |
| *C07K 14/61* | (2006.01) |
| *G16H 50/30* | (2018.01) |

(52) U.S. Cl.
CPC .......... *G16H 20/10* (2018.01); *A61K 38/27* (2013.01); *C07K 14/61* (2013.01); *G16H 10/60* (2018.01); *G16H 50/30* (2018.01)

(58) Field of Classification Search
CPC ...................................................... G16H 20/10
See application file for complete search history.

(56) References Cited

U.S. PATENT DOCUMENTS

| | | | |
|---|---|---|---|
| 7,473,560 B2 | 1/2009 | Soldin | |
| 8,034,627 B2 | 10/2011 | Holmquist et al. | |
| 8,916,385 B2 | 12/2014 | Goldman et al. | |
| 9,034,653 B2 | 5/2015 | Holmquist et al. | |
| 2003/0036923 A1* | 2/2003 | Waldon | G06F 19/3456 705/2 |
| 2003/0175329 A1* | 9/2003 | Azarnoff | A61K 9/0014 424/449 |
| 2010/0023344 A1* | 1/2010 | Hyde | A61K 31/56 705/2 |
| 2011/0190201 A1 | 8/2011 | Hyde et al. | |
| 2012/0101847 A1* | 4/2012 | Johnson | G06Q 10/00 705/3 |
| 2014/0297315 A1 | 10/2014 | Ma et al. | |
| 2017/0173060 A1 | 6/2017 | Schentag et al. | |
| 2018/0272142 A1 | 9/2018 | Zhang et al. | |

OTHER PUBLICATIONS

Gaedigk et al., "The Pharmacogene Variation (PharmVar) Consortium: Incorporation of the Human Cytochrome P450 (CYP) Allele Nomenclature Database", Clinical Pharmacology & Therapeutics, vol. 103 No. 3, Mar. 2018, pp. 399-401.

(Continued)

*Primary Examiner* — John A Pauls
(74) *Attorney, Agent, or Firm* — Thompson Coburn LLP

(57) ABSTRACT

Disclosed herein are a number of techniques that systematically integrate a person's biochemical, symptomatic, and genetic status to generate recommended hormone therapy treatment prescriptions.

46 Claims, 21 Drawing Sheets

(56) References Cited

OTHER PUBLICATIONS

Zanger et al., "Cytochrome P450 Enzymes in Drug Metabolism: Regulation of Gene Expression, Enzyme Activities, and Impact of Genetic Variation", Pharmacology & Therapeutics, 2013, pp. 103-141, vol. 138.
International Search Report and Written Opinion for PCT/US19/55677 dated Jan. 8, 2020.

* cited by examiner

| Formula Number | Relative Concentrations of Estrogen and Progesterone | | FORMULATION |
|---|---|---|---|
| | BIEST (Estrogen) DOSAGE | PROGESTERONE DOSAGE | |
| 1 | LOW | HIGH | Bi-Est 0.2 mg per 0.5 mL; Progesterone 50 mg per 0.5 mL |
| 2 | EQUAL | EQUAL | Bi-Est 1 mg per 0.5 mL; Progesterone 40 mg per 0.5 mL |
| 3 | HIGH | LOW | Bi-Est 2 mg per 0.5 mL; Progesterone 20 mg per 0.5 mL |

410

Values for Progesterone Deficiency Factor (710)

|    | 0   | 12  | 24  | 36  | 48  | 60  | 72  | 84  | 96  | 108 | 120 |
|----|-----|-----|-----|-----|-----|-----|-----|-----|-----|-----|-----|
| 50 | 3,2 | 3,2 | 3,2 | 3,2 | 3,2 | 2,3 | 2,3 | 2,3 | 2,3 | 2,3 | 2,3 |
| 45 | 3,2 | 3,2 | 3,2 | 3,2 | 2,2 | 2,2 | 2,3 | 2,3 | 2,3 | 2,3 | 2,3 |
| 40 | 3,2 | 3,2 | 3,2 | 2,2 | 2,2 | 2,2 | 2,2 | 2,3 | 2,3 | 2,3 | 2,3 |
| 35 | 3,2 | 3,2 | 2,2 | 2,2 | 2,2 | 2,2 | 2,2 | 2,2 | 2,3 | 2,3 | 2,3 |
| 30 | 3,2 | 3,2 | 2,2 | 2,2 | 2,2 | 2,2 | 2,2 | 2,2 | 2,2 | 2,3 | 2,2 |
| 25 | 3,2 | 2,2 | 2,2 | 2,2 | 2,2 | 2,2 | 2,2 | 2,2 | 2,2 | 1,2 | 1,2 |
| 20 | 3,1 | 2,1 | 2,2 | 2,2 | 2,2 | 2,2 | 2,2 | 2,2 | 2,2 | 1,2 | 1,2 |
| 15 | 2,1 | 2,1 | 2,1 | 2,2 | 2,2 | 2,2 | 2,2 | 2,2 | 1,2 | 1,2 | 1,2 |
| 10 | 2,1 | 2,1 | 2,1 | 2,1 | 2,2 | 2,2 | 2,2 | 1,2 | 1,2 | 1,2 | 1,2 |
| 5  | 2,1 | 2,1 | 2,1 | 2,1 | 2,2 | 2,2 | 1,2 | 1,2 | 1,2 | 1,2 | 1,2 |
| 0  | 0,0 | 2,1 | 2,1 | 2,1 | 2,1 | 1,1 | 1,2 | 1,2 | 1,2 | 1,2 | 1,2 |

702

Values for Estrogen Deficiency Factor (700)

Data in Cells 702:
Formulation #, Dosage

Figure 7F

(e.g., 3,2 = 2 doses of Formulation 3)

— 850

**Please rate the severity of your experience with the following symptoms
(0% - least severe; 100% - most severe)**

Anxiety: [25%] — 852

Crankiness: [70%] — 852

Pain or Lumpiness in Breasts: [25%] — 852

Unexplained Weight Gain: [70%] — 852

Insomnia: [25%] — 852

Cyclical Headaches: [70%] — 852

Clear (856)      Next (854)

Figure 8C

Please rate the severity of your experience with the following symptoms
(0% - least severe; 100% - most severe)

Vaginal Dryness: — 25% — 862
Painful Intercourse: — 70% — 862
Hot Flashes: — 25% — 862
Night Sweats: — 70% — 862
Lethargy and Depression: — 25% — 862

Back (868) | Clear (866) | Submit (864)

Patient: Jane Doe
DOB: mm/dd/yyyy
Address: 123 Main Street, Anytown, USA

— 872

Biochemical Status:
Measurement Date: mm/dd/yyyy
Measurement Type: Blood
Progesterone Measurement: VALUE
Estrogen Measurement: VALUE

— 874

Symptomatic Status:

Progesterone Deficiency:
Reporting Date: mm/dd/yyyy
Overall Symptoms Score: VALUE
Anxiety: 75%
Crankiness: 70%
Pain or Lumpiness in Breasts: 33%
Unexplained Weight Gain: 50%
Insomnia: 60%
Cylical Headaches: 75%

Estrogen Deficiency:
Reporting Date: mm/dd/yyyy
Overall Symptoms Score: VALUE
Vaginal Dryness: 25%
Painful Intercourse: 25%
Hot Flashes: 33%
Night Sweats: 10%
Lethargy/Depression: 50%

— 876

Genetic Status:
CYP-1A1: Not Present
CYP-1A2: Not Present
CYP-1B1: Present
BRACA: NOT PRESENT

— 878

Recommendation:  Formulation X, Dosage Y

— 880

Reject (884)    Approve (882)

Figure 8E

| Formula Number | Relative Concentrations of Estrogen and Progesterone | | TESTOSTERONE DOSAGE | FORMULATION |
|---|---|---|---|---|
| | BIEST (Estrogen) DOSAGE | PROGESTERONE DOSAGE | | |
| 1 | LOW | HIGH | - | Bi-Est 0.2 mg per 0.5 mL; Progesterone 50 mg per 0.5 mL |
| 2 | EQUAL | EQUAL | - | Bi-Est 1 mg per 0.5 mL; Progesterone 40 mg per 0.5 mL |
| 3 | HIGH | LOW | - | Bi-Est 2 mg per 0.5 mL; Progesterone 20 mg per 0.5 mL |
| 4 | LOW | HIGH | LOW | Bi-Est 0.2 mg per 0.5 mL; Progesterone 50 mg per 0.5 mL; Testosterone 3 mg per 0.5 mL |
| 5 | EQUAL | EQUAL | LOW | Bi-Est 1 mg per 0.5 mL; Progesterone 40 mg per 0.5 mL; Testosterone 3 mg per 0.5 mL |
| 6 | HIGH | LOW | LOW | Bi-Est 2 mg per 0.5 mL; Progesterone 20 mg per 0.5 mL; Testosterone 3 mg per 0.5 mL |
| 7 | LOW | HIGH | HIGH | Bi-Est 0.2 mg per 0.5 mL; Progesterone 50 mg per 0.5 mL; Testosterone 9 mg per 0.5 mL |
| 8 | EQUAL | EQUAL | HIGH | Bi-Est 1 mg per 0.5 mL; Progesterone 40 mg per 0.5 mL; Testosterone 9 mg per 0.5 mL |
| 9 | HIGH | LOW | HIGH | Bi-Est 2 mg per 0.5 mL; Progesterone 20 mg per 0.5 mL; Testosterone 9 mg per 0.5 mL |

Figure 10E

Please rate the severity of your experience
with the following symptoms
(0% - least severe; 100% - most severe)

Decreased Libido: [25%] — 1052
Chronic Fatigue: [79%] — 1052
Painful Intercourse: [25%] — 1052
Dry Skin: [79%] — 1052
Loss of Muscle Tone in Arms and Legs: [25%] — 1052

Back (1058)   Clear (1056)   Submit (1054)

APPLIED ARTIFICIAL INTELLIGENCE TECHNOLOGY FOR HORMONE THERAPY TREATMENT

CROSS-REFERENCE AND PRIORITY CLAIM TO RELATED PATENT APPLICATIONS

This patent application claims priority to U.S. provisional patent application Ser. No. 62/745,756, filed Oct. 15, 2018, and entitled "Applied Artificial Intelligence Technology for Hormone Therapy Treatment", the entire disclosure of which is incorporated herein by reference.

This patent application is also a continuation of PCT patent application PCT/US2019/055677, designating the US, filed Oct. 10, 2019, and entitled "Applied Artificial Intelligence Technology for Hormone Therapy Treatment", which claims priority to U.S. provisional patent application Ser. No. 62/745,756, filed Oct. 15, 2018, and entitled "Applied Artificial Intelligence Technology for Hormone Therapy Treatment", the entire disclosures of each of which are incorporated herein by reference.

INTRODUCTION

Many people suffer from health complications that arise from hormone deficiencies, particularly people at older ages. The inventor believes that conventional medical treatments which aim to alleviate the adverse effects of hormone deficiencies heavily rely on highly imprecise, "rule of thumb" decision-making by doctors.

For example, FIG. 1A shows an example process flow for conventional hormone therapy treatment using FDA-approved drugs. At step 100, the doctor asks the patient about symptoms that are associated with a hormone deficiency. At step 102, the doctor applies his or her knowledge and experience to decide on an appropriate FDA-approved hormone therapy treatment for the patient in view of the patient's responses to the doctor's questions about symptoms. This treatment will take the form of some formulation of an FDA-approved hormone therapy treatment (e.g., an identification of an FDA-approved hormone drug or an identification of an FDA-approved mix of multiple hormone drugs) and a dosage for that formulation (e.g., how much of the formulation to administer each day). At step 104, the doctor writes a prescription for the patient in accordance with the treatment decision made at step 102. The patient then takes this prescription to a pharmacy to be filled (step 106). At step 108, the pharmacy fills the prescription, and the patient then administers the hormone therapy treatment using the filled prescription (step 110).

This conventional approach to hormone therapy treatment continues during follow-ups between the patient and doctor, as shown by FIG. 1B. During a follow-up consultation after the patient has undergone hormone therapy treatment as prescribed by FIG. 1A, the doctor will then ask the patient about whether the symptoms have improved or gotten any worse (step 120). Based on the patient's feedback at step 120, the doctor once again applies his or her knowledge and experience to decide on an appropriate hormone therapy treatment (step 122), which may include an adjustment of some sort based on the patient answers to the follow-up questions. At step 124, the doctor writes a new hormone therapy treatment prescription for the patient based on the decision at step 122. The patient then gets the new prescription filled (steps 126 and 128) so that the treatment in accordance with the new prescription can be administered (step 130).

It is not routine or typical for doctors to measure the patient's hormone levels prior to prescribing FDA-approved hormone therapy treatments to their patients. However, when prescribing bio-identical hormones as part of a hormone therapy treatment, many doctors do so after the patient's hormone levels have been measured (typically, via a saliva sample). But, even when prescribing customized hormone therapy treatments for patients after reviewing the patients' measured hormone levels, the inventor believes that doctors are still routinely using only their own general ad hoc knowledge to arrive at a prescribed course of action.

When these conventional approaches for hormone therapy treatment are repeated for multiple patients and multiple doctors, the result is that large volumes of patients are being prescribed hormone therapy treatment in a highly de-centralized, un-systematic manner, which results in thousands and thousands of highly differentiated hormone therapy treatment prescriptions, even to patients in similar situations with respect to their hormone deficiencies. This is particularly a problem with customized treatments that arise after hormone measurements because the measurement-derived customizations introduce a virtually limitless number of variations in potential hormone therapy treatment prescriptions. Further still, the inventor believes that many doctors who prescribe hormone therapy treatments for patients develop their "favorite" hormone formulations that then get tweaked in small fashions when the doctors decide on a specific prescription for a given patient. This results in compounding pharmacies filling prescriptions for thousands of different hormone formulations, which increases costs for patients because of the lack of mass production opportunities for hormone formulations (due to the large number of small variations between different prescribed formulations) while not achieving measurable improvements in effectiveness.

The inventor believes that improvements are needed in how hormone therapy treatments are prescribed and administered. Toward this end, the inventor discloses a number of practical applications of computer technology that systematically integrate a person's biochemical, symptomatic, and genetic status to generate recommended hormone therapy treatment prescriptions for the person.

To obtain data about a person's biochemical status, the person in an example embodiment can provide a biological sample (e.g., a bodily fluid sample, such as blood, saliva, serum, plasma sample, and/or urine) so that measurements of the hormones of interest can be obtained. For example, the system can quantify measurements of how much of Hormone 1 and Hormone 2 are present in the person's blood. This measurement data can then represent the person's biochemical status.

To obtain data about a person's symptomatic status, the person in an example embodiment can interact with an application (such as a mobile application or web application) to provide the system with data that represents the extent of symptoms experienced by the person with respect to deficiencies of hormones of interest. For example, if there are 5 known symptoms of a deficiency of Hormone 1, the application can prompt the person for input that quantifies the severity of these symptoms as experienced by the person; and if there are 10 known symptoms of a deficiency of Hormone 2, the application can also prompt the person for input that quantifies the severity of these symptoms as experienced by the person. The inputs through the application can then represent the person's symptomatic status.

To obtain data about a person's genetic status, the person in an example embodiment can provide a genetic sample (e.g., a bodily fluid sample, such as blood, saliva, serum, plasma sample, and/or urine; a hair sample, a skin sample, or any other biological sample that can be used to establish a person's genetic profile) so that the person's genetic profile can be determined. For some people, this genetic testing may have already occurred prior to seeking hormone therapy treatment and their genetic profiles may be available electronically prior to seeking hormone therapy treatment. For other people, the genetic testing may occur as part of the hormone therapy treatment process. The person's genetic profile can then represent the person's genetic status.

The computer technology can then systematically integrate the data representing the person's biochemical, symptomatic, and genetic status using a new and innovative programmatic function that translates this data into a recommended hormone therapy treatment prescription. In a dramatic departure from the routine and conventional approaches for hormone therapy treatment where doctors apply ad hoc rules of thumb based on the patient's reported symptoms (and perhaps measured hormone levels) to arrive at a course of treatment, this new and innovative programmatic function allows for a normalization of treatment across large populations of patients (because the same programmatic function would be used for large populations of patients) while still allowing for highly personalized, patient-specific treatments. In doing so, the computer technology does significantly more than merely automate the process flows of FIGS. 1A and 1B. First, the conventional approach to prescribing hormone therapy treatments does not rely the person's genetic makeup. Second, the computer technology leverages new quantified relationships between data values and data elements, where these relationships were not considered by doctors using routine and known treatment decision-making. Third, the computer technology provides a level of systematized normalization that was not possible via the de-centralized decision-making shown by FIGS. 1A and 1B. As such, data can be more accurately tracked over time and optionally across large patient populations to permit feedback loops that improve upon the analysis performed by the computer system and optimize how a person's biochemical, symptomatic, and genetic status gets translated into a recommendation of a specific hormone therapy treatment. For at least these and other reasons, the computer technology described herein does significantly more than merely encode doctors' pre-existing techniques, and it represents a pioneering and groundbreaking new manner of facilitating hormone therapy treatment for patients.

In an example embodiment, the inventor discloses that the computer system can maintain a data structure that associates a plurality of different prescriptions of a formulation of first and second hormones with a first deficiency factor associated with the first hormone and a second deficiency factor associated with the second hormone. This data structure embodies a new and innovative manner of relating different hormone therapy treatment prescriptions with data representative of quantified hormone deficiencies. The inventor further discloses a new and innovative programmatic function that can compute a first hormone deficiency factor value and a second hormone deficiency factor value that quantifies the person's hormone deficiencies based on the person's biochemical, symptomatic, and genetic status. These computed hormone deficiency factors are new data points that provide actionable intelligence about the person that go beyond mere diagnosis because the computed hormone deficiency factors are scaled in a manner that links them in an automatable fashion to different treatment options. The computer system can then select a recommended hormone therapy treatment prescription for the person by looking up in the data structure which prescription is associated with the computed first and second hormone factor values.

In other example embodiments, the analysis performed by the computer system to recommend hormone therapy prescriptions can also take into consideration other data about the person. For example, a person's body fat composition characteristic (e.g., a body mass index (BMI), body fat percentage (BFP), or other measure that is indicative of a person's body fat composition) can be used to influence how the computer system selects a recommended prescription. This also represents a vast improvement over conventional approaches to hormone therapy treatment because the conventional approaches do not systematically consider such data elements. As another example, a patient's medication history can be used to influence how the computer system selects a recommended prescription. As yet another example, a patient's surgical history can be used to influence how the computer system selects a recommended prescription.

Further still, the techniques described herein can be extended to prescriptions of a single hormone or more than 2 hormones. For example, the prescription may include a formulation of 3 or more hormones, and the programmatic function can also leverage the person's biochemical, symptomatic, and genetic status to arrive at an appropriate recommended prescription of 3 hormones.

Moreover, techniques for tracking patient data and prescriptions over time allows for innovative feedback techniques whereby treatments and analysis can be improved over time.

In example embodiments discussed below, the hormones of interest are progesterone and estrogen to help treat women who are undergoing peri-menopause, menopause, or other conditions affecting and/or affected by their female hormone levels. However, it should be understood that these hormones are just examples; and the technology described herein can be applied to other hormones and other types of patients if desired by a practitioner. In certain embodiments, the hormones of interest are thyroid hormones (e.g., thyroxine (T4) and/or triiodothyronine (T3)) and/or Thyroid-Stimulating Hormone (TSH) and the technology described herein is applied to patients with thyroid hormone-associated disorders (e.g., hyperthyroidism or hypothyroidism).

These and other features and advantages of the present invention will be described hereinafter to those having ordinary skill in the art.

BRIEF DESCRIPTION OF THE DRAWINGS

FIGS. 7A-7F depict examples of data structures that can be used for associating prescription options with various values of deficiency factors for the first and second hormones.

FIGS. 8C and 8D depict example user interfaces for the mobile application of FIGS. 8A and 8B.

FIG. 8E depicts an example user interface for use by a doctor to interact with the system.

FIGS. 10D and 10E depict examples of data structures that can be used for associating prescription options with various values of deficiency factors for the first, second, and third hormones.

FIG. 10F depicts an example user interface for a mobile application to collect symptom experience data from a patient relating to deficiencies of a third hormone.

DETAILED DESCRIPTION OF EXAMPLE EMBODIMENTS

Figures 1A, 1B:
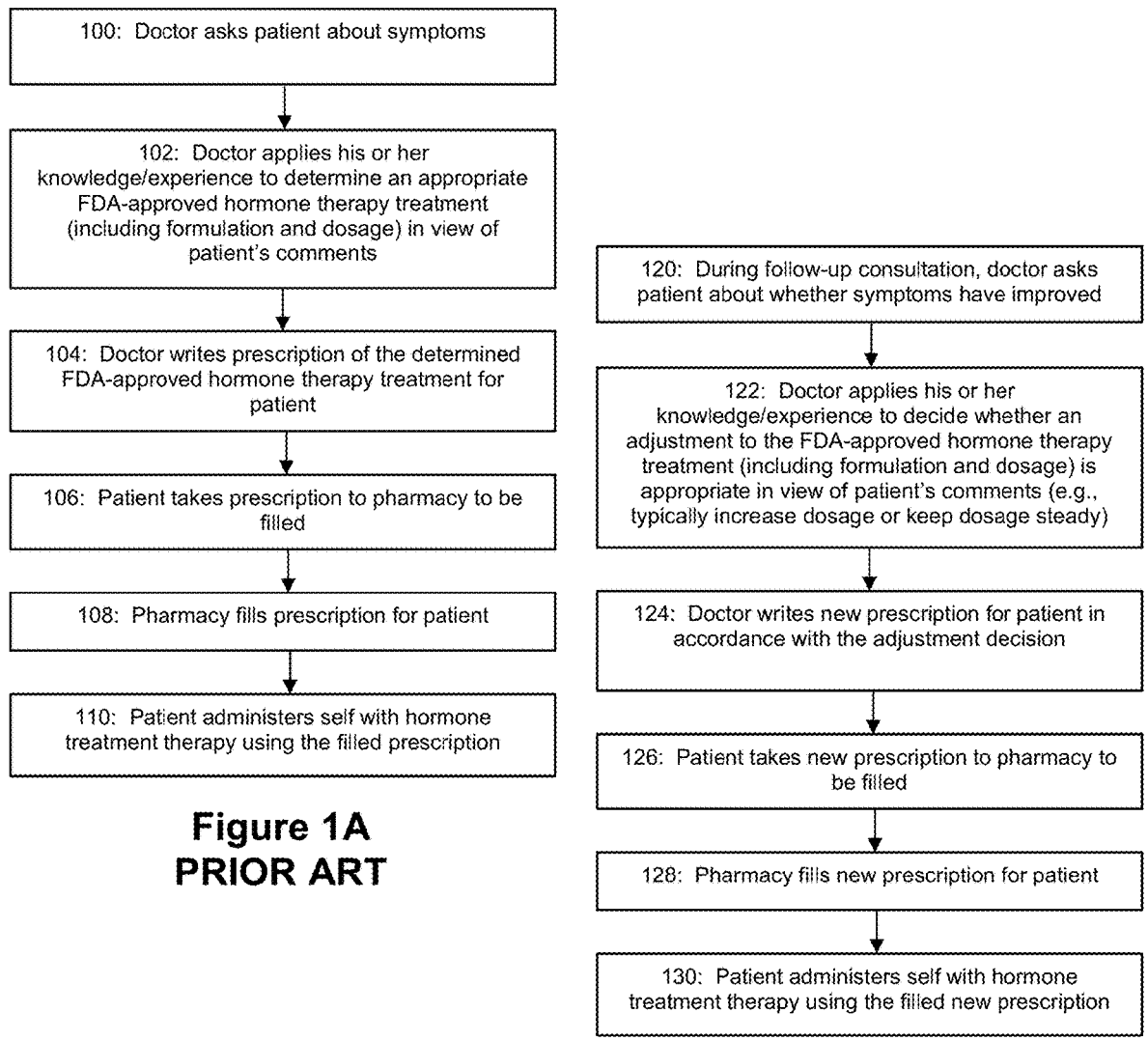
FIGS. 1A and 1B show conventional processes for hormone treatment therapy.
Figure 2:
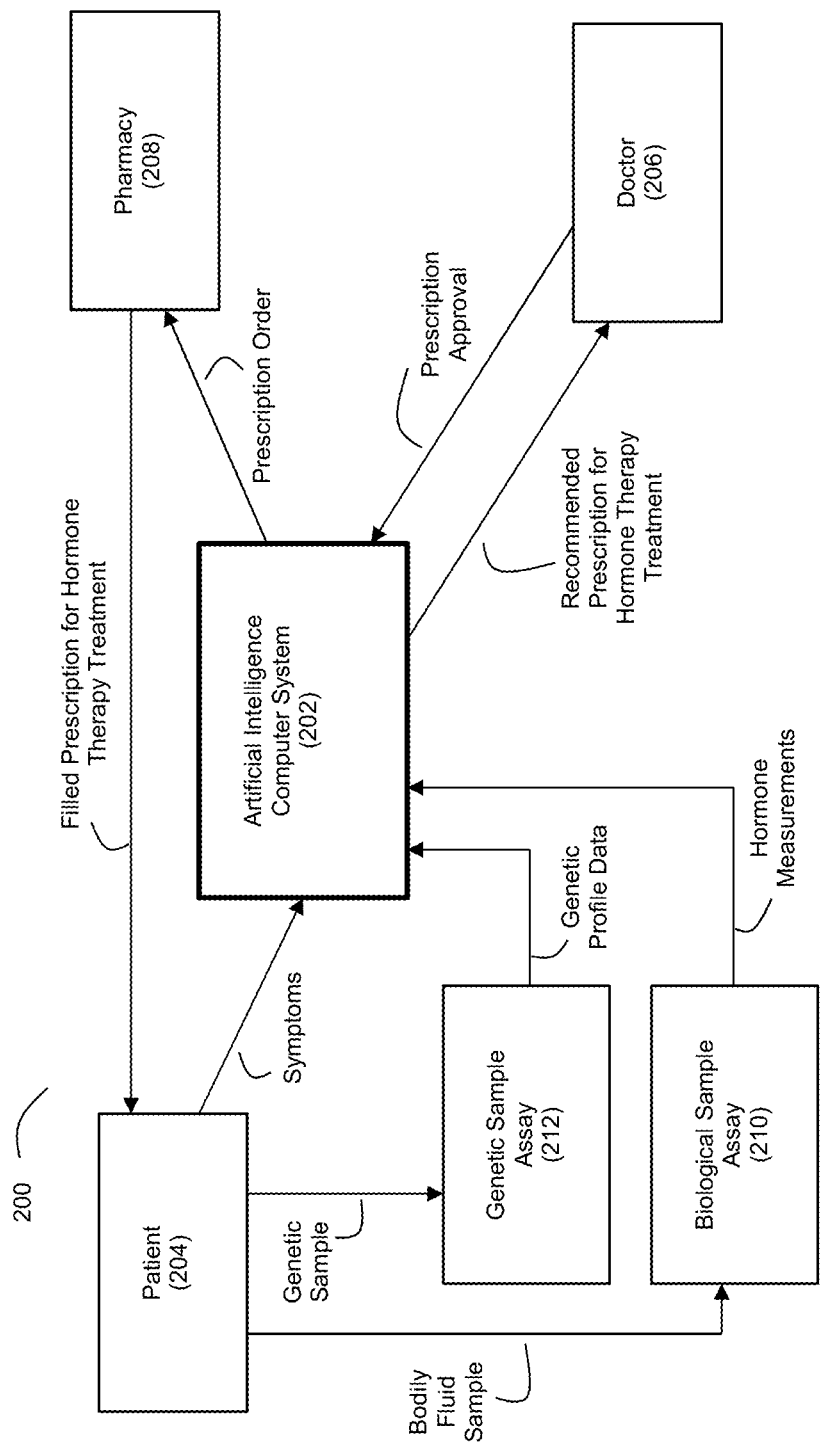
FIG. 2 depicts an example treatment system in accordance with an example embodiment.

FIG. 2 depicts an example treatment system 200 in accordance with an example embodiment. The system 200 includes an artificial intelligence (AI) computer system 202 that interacts with one or more patients 204, one or more doctors 206, one or more pharmacies 208, one or more biological sample assays 210, and one or more genetic sample assays 212 to compute a recommended prescription for hormone therapy treatment with respect to patient 204 based on the patient's biochemical, symptomatic, and genetic status.

The biological sample assay 210 can be administered by a testing company on a biological sample such as a bodily fluid sample provided by the patient 204. Examples of suitable bodily fluids that can be used for the sample include blood, saliva, serum, plasma sample, and/or urine. From this assay 210, the hormone measurements for the patient 204 can be obtained (e.g., the level of Hormone 1 in the patient 204 and the level of Hormone 2 in the patient 204). For purposes of discussion, the examples discussed below will presume that the measured hormone levels constitute measured levels of the subject hormone's in the patient's blood. In certain embodiments, a subject hormone that is measured will comprise one or more biologically active forms of the hormone. In certain embodiments where estrogen levels are determined, one or more of estrone (E1), estradiol (E2 or 17-beta-estradiol), and/or Estriol (E3) can be measured. Measurements of hormone levels can be obtained by any suitable method including immunological and mass spectrometry-based methods. Various mass spectrometry based methods disclosed in U.S. Pat. Nos. 7,473,560, 8,034,627, 8,916,385, and 9,034,653, each of which is specifically incorporated herein by reference in their entireties, can be used to measure hormones. Data representing these hormone measurements can then be communicated to the computer system 202.

The genetic sample assay 212 can be administered by a testing company on a genetic sample provided by the patient 204. Examples of suitable genetic samples can include bodily fluids (e.g., blood, saliva, serum, plasma sample, and/or urine), hair samples, skin samples, and the like. From this assay 212, the genetic profile for the patient 204 can be obtained. An example of genetic information that can be useful for system 200 include indicators as to whether the patient's has any genes that are known (or believed) to affect a person's metabolism of administered hormones. Additional examples of genetic information that can be useful for system 200 include indicators as to whether the patient has any genes that show a predisposition for certain types of cancers (e.g., breast cancer, ovarian cancer, cervical cancer, uterine cancer, and/or other cancers that are metastatic and/or known (or believed) to possess steroid-responsive cell types. Data representing the patient's genetic profile can then be communicated to the computer system 202. It should be understood that because a patient's genetic profile is not expected to change over time, the genetic testing via assay 212 need not be performed contemporaneously with the hormone therapy treatments. For example, a patient 204 may have a pre-existing genetic profile that can be communicated to the computer system 202, where this genetic profile was created from an assay 212 long in the past.

The patient 204 can provide data to the computer system 202, where this data quantifies any hormone deficiency symptoms experienced by the patient 204. An application such as a mobile application and/or a web application can be made available to the patient 204 to provide the patient 204 with an effective mechanism for communicating such symptom data to the computer system 202. In addition to symptom data, the patient 204 may also provide the computer system 202 with other patient information, such as patient medical data (e.g., fat composition characteristic data such as BMI or BFP, cancer history, medication history, and/or surgical history). In certain embodiments, genetic, medication, or surgical history of a $1^{st}$ degree relative could be used.

Using the data obtained from the patient 204 and assays 210 and 212, the computer system 202 produces a recommended hormone therapy treatment prescription. This prescription can identify a formulation of a first and second hormone including their relative concentrations. The prescription can also identify a dosage for the formulation. In stating that the hormone therapy treatment includes a formulation of two hormones, it should be understood that the hormones in the formulation can take the form of the subject hormone itself or one or more biologically active forms thereof, an analog thereof, a precursor thereof, and/or a metabolite thereof. Thus, in an example where the formulation includes estrogen, the formulation may include a mixture of estradiol and estrone (e.g., a mixture of about 80% estradiol and about 20% estriol by weight). The computer system 202 can then communicate its prescription recommendations to a doctor 206. Upon approval of the recommended prescription by the doctor 206, the computer system 202 can then place a prescription order with a pharmacy 208. The computer system 202 can utilize any of a number of electronic communication mechanisms for interfacing with the doctor 206 and pharmacy 208. For example, an application such as a mobile application and/or web application can be made available to the doctor 206 for reviewing the recommended prescriptions and providing approvals/rejections thereof. To interface with the pharmacy 208, an electronic link such as a web services communication link with an electronic business system maintained by the pharmacy 208 can be employed.

The pharmacy 208 then fills the ordered prescription, and the patient 204 then obtains the filled prescription from the pharmacy 208. Thereafter, the patient 204 can administer the prescribed hormone therapy treatment. Once that prescribed treatment has been completed, the process can be repeated as may be necessary to continue the hormone therapy treatment for the patient 204.

Accordingly, the system 200 of FIG. 2 can be put into beneficial use by any of a number of different parties. Patients 204 can interact with the system 200 in order to obtain hormone therapy treatments that may relieve various symptoms of hormone deficiencies. Doctors 206 can interact with the system 200 in order to more efficiently provide health care services to patients 204. Pharmacies 208 can interact with the system 200 in order to increase the volume of prescription fills for patients and thereby increase revenues. Any testing companies that perform tests with respect to assays 210 and 212 can interact with the system 200 in order to increase the volume of testing they perform and thereby increase revenues. Furthermore, given that effective hormone therapy treatment via system 200 will likely involve follow-up testing of biological sample assays 210 so that the system can track patient's hormone levels over time and assess whether treatments are working, the system 200 can thus serve as a potential source of recurring revenue for testing companies.

Figure 3:
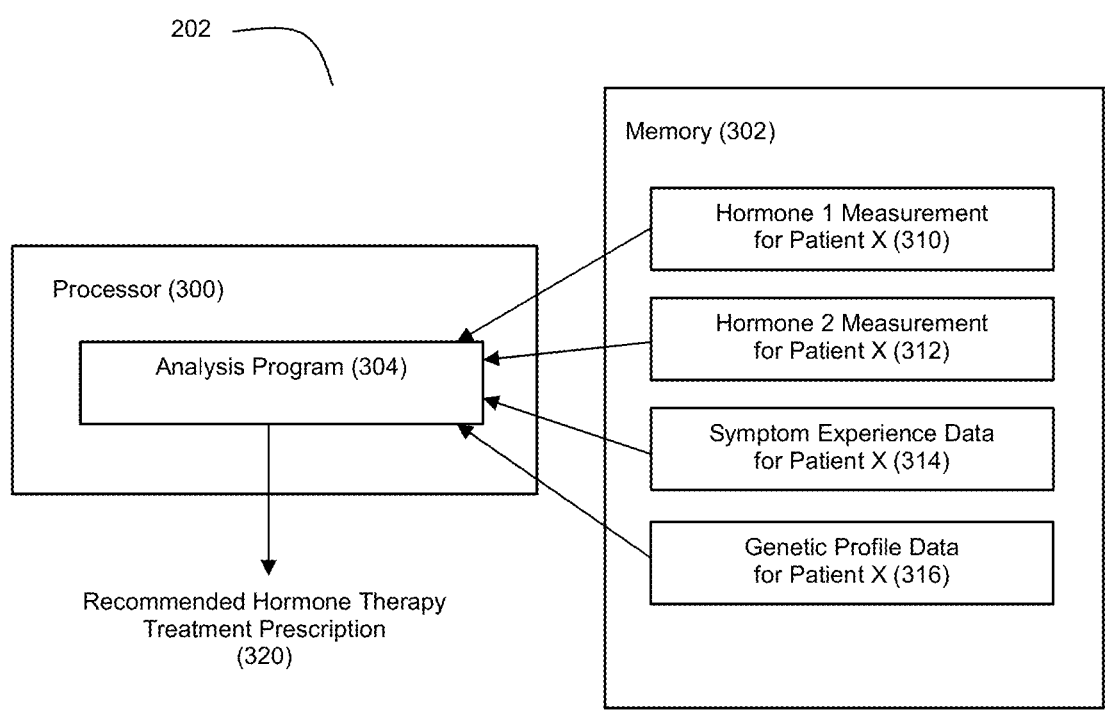
FIG. 3 depicts an example computer system for use with the treatment system of FIG. 2 to recommend a hormone therapy treatment prescription of first and second hormones.

The AI computer system 202 can take the form of one or more servers that are configured for electronic communication via networks such as the Internet and/or wireless telecommunications networks with the patients 204, testing companies, doctors 206, and/or pharmacies 208. Such a computer system 202 may take the form of a distributed computing system with multiple servers that are operatively linked via networked communications to provide the features described herein; for example, cloud-based servers. FIG. 3 depicts an example embodiment for computer system 202, where the computer system includes a processor 300 and memory 302 that are operatively linked. It should be understood that the processor 300 may include multiple processors that perform the operations described herein in a distributed manner. It should also be understood that memory 302 can be a distributed memory.

Memory 302 can store various data about the patient 204 as discussed above. For example, memory 302 can store data 310 that represents a measurement for a first hormone in the patient 204 (as derived from assay 210). Memory 302 can also store data 312 that represents a measurement for a second hormone in the patient 204 (as derived from assay 210). Memory 302 can also store symptom experience data 314 that represents a quantification of any symptoms associated with deficiencies of the first and second hormones by the patient 204. Further still, memory 302 can store genetic profile data 316 for the patient 204 (as derived from assay 212).

Figure 4A:
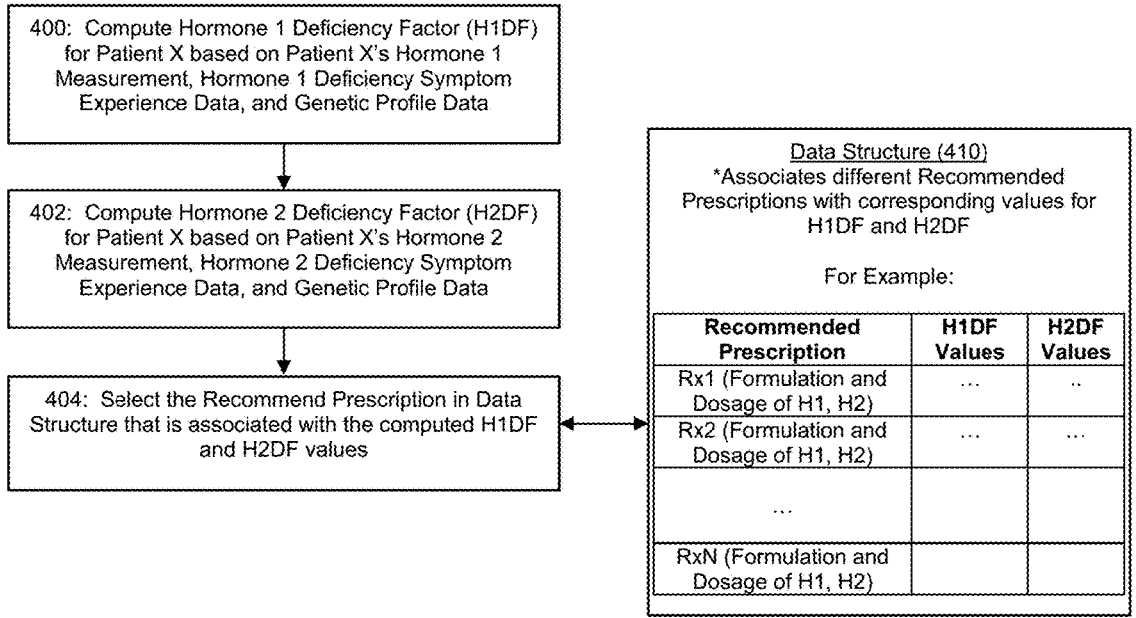
FIG. 4A depicts an example process flow for execution by a computer system to recommend hormone therapy treatment prescriptions of first and second hormones.

Processor 300 can then execute an analysis program 304 that systematically integrates data 310, 312, 314, and 316 to compute a recommended hormone therapy treatment prescription 320. Analysis program 304 can be embodied by a plurality of processor-executable instructions that are resident in a non-transitory computer-readable storage medium such as computer memory. FIG. 4A depicts an example process flow for program 304. In this example, the hormone therapy treatment will evaluate deficiencies of Hormone 1 (H1) and Hormone 2 (H2).

With reference to FIG. 4A, at step 400 the processor computes an H1 deficiency factor (H1DF) for Patient X based on Patient X's H1 measurement (see data 310), H1 deficiency symptom data (see data 314), and genetic profile data (see data 316). At step 402, the processor computes an H2 deficiency factor (H2DF) for Patient X based on Patient X's H2 measurement (see data 312), H2 deficiency symptom data (see data 314), and genetic profile data (see data 316). Examples of techniques that can be used for computing H1DF and H2DF are discussed below.

The computer system 202 can also maintain a data structure 410 in memory 302, where this data structure 410 associates different options for recommended prescriptions of H1 and H2 with corresponding values for H1DF and H2DF. For example, this data structure 410 can take the form of a lookup table where different prescriptions of H1 and H2 (e.g., Rx1 with a particular formulation and dosage of H1 and H2, Rx2 with a particular different formulation and dosage of H1 and H2, etc. through R—N) are linked to associated values of H1DF and H2DF. Using these computed H1DF and H2DF values, the processor can select the prescription that is to be recommended for the patient (see Step 404 in FIG. 4A). While data structure 410 is described as a look-up table such as a grid in example embodiments below, it should be understood that other types of data structures such as arrays, linked lists, or any other data structure suitable for associating prescription recommendations with H1DF and H2DF values that can be used by computer system 202.

Figure 4B:
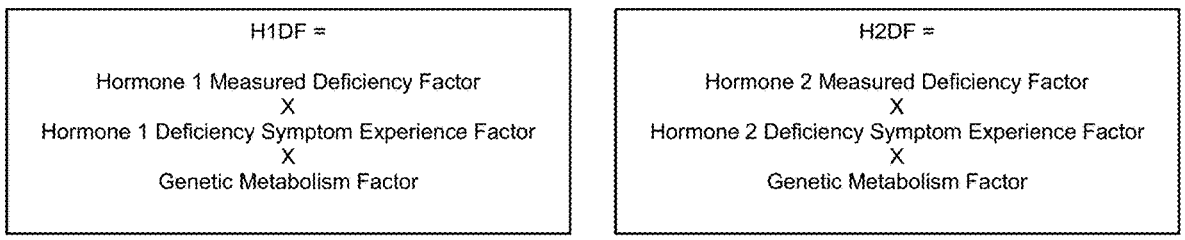
FIGS. 4B and 4C depict examples of how first and second hormone deficiency factors can be systematically computed based on a person's biochemical, symptomatic, and genetic status.

FIG. 4B shows examples of functions that can be used by program 304 to compute H1DF and H2DF. H1DF can be computed as function of an H1 Measured Deficiency Factor, an H1 Deficiency Symptom Experience Factor, and a Genetic Metabolism Factor. For example, H1DF can be computed as the product of the H1 Measured Deficiency Factor, the H1 Deficiency Symptom Experience Factor, and the Genetic Metabolism Factor. H2DF can be computed as function of an H2 Measured Deficiency Factor, an H2 Deficiency Symptom Experience Factor, and the Genetic Metabolism Factor. For example, H2DF can be computed as the product of the H2 Measured Deficiency Factor, the H2 Deficiency Symptom Experience Factor, and the Genetic Metabolism Factor.

In an example embodiment, the H1 Measured Deficiency Factor (H1MDF) can be computed according to an inverse relationship with the measured level of H1 for the subject patient from assay 210. Thus, in an example embodiment, H1MDF can be computed as:

$$H1MDF = \frac{1}{[H1M]} \qquad \text{Equation (1)}$$

where H1M represents the measured level of H1 from assay 210. The value for H1M can be included as part of data 310 (see FIG. 3).

In an example embodiment, the H1 Deficiency Symptom Experience Factor (H1DSEF) can be computed as an aggregation of severity data experienced by the subject patient for different symptoms of an H1 deficiency. Thus, in an example embodiment, H1DSEF can be computed as:

$$H1DSEF = \Sigma_{i=1}^{N}(H1_S)_i \qquad \text{Equation (2)}$$

where N represents the total number of different symptoms associated with an H1 deficiency, and where $(H1_S)_i$ represents the user-specified severity value for symptom i associated with an H1 deficiency. The values for $(H1_S)_i$ can be included as part of data 314 (see FIG. 3).

In an example embodiment, the Genetic Metabolism Factor (GMF) can be computed according a function that operates to scale the other factors based on the presence of certain genes linked to an effect on steroid hormone metabolism in humans. For example, steroid hormones, including the sex steroids, are metabolized primarily by the Cytochrome P450 (CP450) family of genes, primarily CYP-1A1 and CYP-1A2 and to a lesser extent CYP-1B1. Polymorphisms of these genes can dramatically affect (increase or decrease) a person's metabolism of endogenous and exogenous hormones. Accordingly, if the patient's genetic profile indicates the presence of an allele of the CP450 family of genes in the patient associated with more rapid metabolism (i.e., catabolism) of one or more hormones, then GMF will upwardly adjust H1DF and H2DF. Thus, in an example embodiment, GMF can be computed as:

$$GMF = 1 + (W1(CYP-1A1) + W2(CYP-1A2) + W3(CYP-1B1)) \qquad \text{Equation (3)}$$

where CYP-1A1 serves as a presence indicator (e.g., the value will be 0 if not present and 1 if present) for the patient with respect to an allelic status of CYP-1A1 in the patient, where CYP-1A2 serves as a presence indicator for the patient with respect to an allelic status of CYP-1A2 in the patient, and where CYP-1B1 serves as a presence indicator for the patient with respect to an allelic status of CYP-1B1 in the patient. The values for CYP-1A1, CYP-1A2, and CYP-1B1 can be included as part of data 316 (see FIG. 3). Furthermore, the values for W1, W2, and W3 can serve as weights that control how much of an effect the various gene indicators will have on GMF. W1 can define a weight for the CYP-1A1 presence indicator, W2 can define a weight for the CYP-1A2 presence indicator, and W3 can define a weight for the CYP-1B1 presence indicator. Non-limiting examples of CYP1A1, CYP1A2, and CYP1B1 alleles associated with more rapid metabolism of one or more hormones include those set forth in the National Center for Biotechnology Information (NCBI) world wide web site "ncbi.nlm.nih.gov" and the Pharmacogene Variation (PharmVar) Consortium website on the world wide web at "pharmvar.org" (Gaedigk et al. *Clin. Pharm. & Thera.* November 2017 PMID: 29134625doi:10.1002/cpt.910). Since identification of CYP1A1 (NCBI Gene ID: 1543), CYP1A2 (NCBI Gene ID: 1544), and CYP1B1 (NCBI Gene ID: 1545) alleles associated with more rapid metabolism of one or more hormones and population of databases containing the same is ongoing, GMF values can be periodically re-entered (e.g., upon refilling a prescription) in the apparati, systems, computer program products, and methods provided herein. In an example embodiment, the values for W1, W2, and W3 can be 0.2, 0.1. and 0.04 respectively. With such weights, this means that the GMF value can range from 1 (if none of the CYP450 gene alleles are present) to 1.34 (if all of the CYP450 gene alleles are present). While certain members of the CYP450 gene family are discussed in this example, it should be understood that alleles of other CYP450 genes and non-CYP450 genes that are deemed to impact how people metabolize or respond to steroid hormones can also be taken into consideration when computing GMF (including potentially alleles of any genes that are linked to decreased steroid metabolism). It should also be understood that expression levels of the aforementioned CYP450 genes can also be used in computing GMF. Factors including various genetic polymorphisms (e.g., alleles), induction by xenobiotics, regulation by cytokines, hormones and during disease states, as well as the sex and age of a subject can influence CYP450 gene expression (Zanger and Schwab; *Pharmacol Ther.* 2013 April; 138(1):103-41. doi: 10.1016/j.pharmthera.2012.12.007).

Thus, H1DF can be computed in an example embodiment as follows:

$$H1DF = H1MDF \times H1DSEF \times GMF \qquad \text{Equation (4)}$$

$$H1DF = \left(\frac{1}{[H1M]}\right) \times \left(\sum_{i=1}^{N}(H1_S)_i\right) \times$$
$$(1 + (W1(CYP-1A1) + W2(CYP-1A2) + W3(CYP-1B1))) \qquad \text{Equation (5)}$$

H2DF can be computed in a similar fashion, but where H2 measurements and H2 symptom experience data are used. The H2 Measured Deficiency Factor (H2MDF) can be computed according to an inverse relationship with the measured level of H2 for the subject patient from assay 210. Thus, in an example embodiment, H2MDF can be computed as:

$$H2MDF = \frac{1}{[H2M]} \qquad \text{Equation (6)}$$

where H2M represents the measured level of H2 from assay 210. The value for H2M can be included as part of data 312 (see FIG. 3). Likewise, the H2 Deficiency Symptom Experience Factor (H2DSEF) can be computed as an aggregation of severity data experienced by the subject patient for different symptoms of an H2 deficiency. Thus, in an example embodiment, H2DSEF can be computed as:

$$H2DSEF = \Sigma_{i=1}^{M}(H2_S)_i \qquad \text{Equation (7)}$$

where M represents the total number of different symptoms associated with an H2 deficiency, and where $(H2_S)_i$ represents the user-specified severity value for symptom i associated with an H2 deficiency. The values for $(H2_S)_i$ can be included as part of data 314 (see FIG. 3). The same GMF used for computing H1DF can be used when computing H2DF. Accordingly, H2DF can be computed in an example embodiment as follows:

$$H2DF = H2MDF \times H2DSEF \times GMF \qquad \text{Equation (8)}$$

-continued $$H2DF = \left(\frac{1}{[H2M]}\right) \times \left(\sum_{i=1}^{M} (H2_S)_i\right) \times$$

$$(1 + (W1(CYP-1A1) + W2(CYP-1A2) + W3(CYP-1B1)))$$

Equation (9)

Figure 4C:
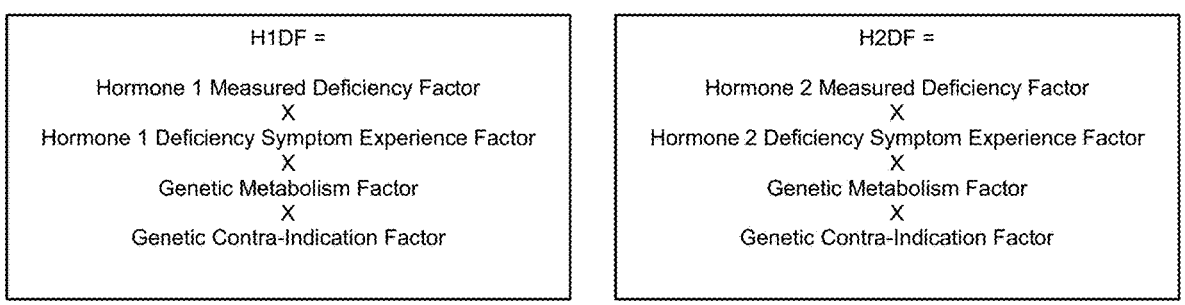

Further still, additional terms can be factored into the H1DF and H2DF computations if desired by a practitioner. An example of this is shown by FIG. 4B. In the example of FIG. 4C, the H1DF and H2DF computations also include a genetic contra-indication factor (GCIF). If the patient's genetic profile shows a predisposition for certain types of cancers (e.g., breast cancer, ovarian cancer, cervical cancer, uterine cancer, and/or other cancers that are metastatic or known (or believed) to possess steroid hormone-responsive cell types (e.g., hormone receptor-positive cells, including estrogen-receptor or progesterone receptor positive cells), this would indicate the patient is not suitable for hormone therapy treatment. For example, loss-of-function alleles of the BRCA1 and BRCA2 tumor suppressor genes are linked to increased risks of breast cancer. Non-limiting examples of BRCA1 and BRCA2 loss-of-function alleles include those set forth in the National Center for Biotechnology Information (NCBI) world wide web site "ncbi.nlm.nih.gov/clinvar." Since identification of BRCA1 (NCBI Gene ID: 672) or BRCA2 (NCBI Gene ID: 675) loss-of-function alleles and population of databases containing the same is ongoing, GCIF values can be periodically re-entered (e.g., upon refilling a prescription). Accordingly, the formulas for H1DF and H2DF may also include a GCIF that operates to zero out the H1DF and H2DF values if the patient's genetic profile data indicates the presence of either the BRCA1 or BRCA2 loss-of-function gene alleles. For example, GCIF can be computed as follows:

$$GCIF=f(BRACA)$$ Equation (10)

where f(BRACA) will be zero the patient's genetic profile data indicates the presence of either the BRCA1 or BRCA2 loss-of-function gene alleles, and where f(BRACA) will be 1 otherwise. The value for BRACA can be included as part of data 316 (see FIG. 3). Thus, with H1DF and H2DF being computed as shown below, it can be seen that H1DF and H2DF will zero out if the patient's genetic profile shows the presence of either the BRCA1 or BRCA2 loss-of-function gene alleles:

$$H1DF=H1MDF \times H1DSEF \times GMF \times GCIF$$ Equation (11)

$$H2DF=H2MDF \times H2DSEF \times GMF \times GCIF$$ Equation (12)

However, it should be understood that such treatment contra-indicators need not be factored directly into the H1DF and H2DF computations if desired by the practitioner. For example, the FIG. 4 process flow could include conditions at the outset where no H1DF or H2DF values will be computed if any contra-indications are present.

Figure 5:
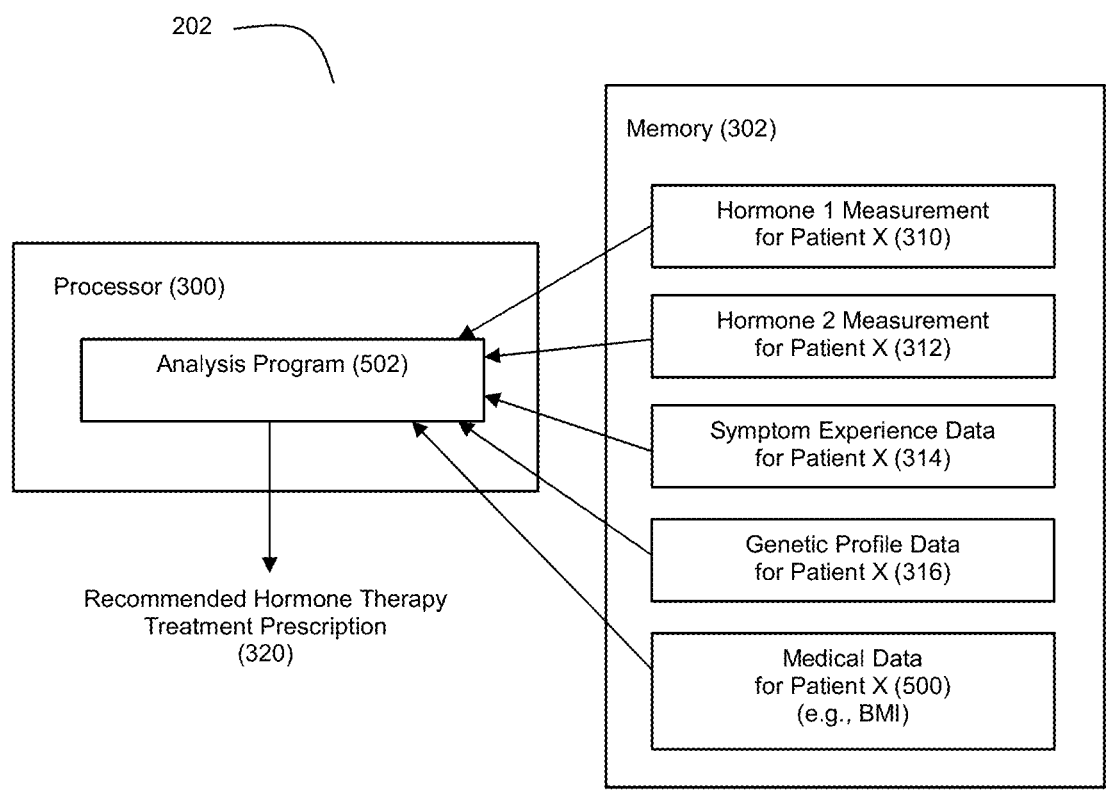
FIG. 5 depicts another example computer system for use with the treatment system of FIG. 2 to recommend a hormone therapy treatment prescription of first and second hormones.

In another example embodiment, the analysis program 304 can also take into consideration additional medical data about the subject patient when recommending hormone therapy treatment prescriptions. For example, as shown by FIG. 5, the memory 302 can also store medical data 500 about the patient, and this data 500 can be used by analysis program 502 when deciding on an appropriate prescription recommendation. As an example, the medical data 500 can be data indicative of the patient's body fat composition (e.g., a BMI or BFP for the patient). Steroid hormones are fat soluble and therefore are deposited within and attain higher concentrations in fatty tissues. Thus, the volume of distribution of hormones is directly proportional to the amount of fat present in the patient. Patients who have higher amounts of fatty tissues are expected to require higher dosages of administered steroid hormones to attain the same active (blood/serum) levels as a person with less fatty tissue. BMI can serve as a measure of a patient's lean vs. fat mass, and can thus be used to establish the relative volume of distribution of fat-soluble drugs, including all steroid hormones. However, it should be understood that medical characteristics other than BMI could be used, such as BFP. In certain embodiments, BFP data obtainable by skinfold caliper, Dual-Energy X-ray Absorptiometry (DXA), hydrostatic weighing, air displacement plethysmography, bioelectric impedance analysis (BIA), bioimpedance spectroscopy (BIS), Electrical Impedance Myography (EIM), 3-D body scans, and multi-compartment models using certain combinations of the aforementioned techniques can be used. Also, the system may use other types of medical information about the patient as medical data 500. For example, a patient's medication history can be used as part of data 500 to influence the analysis program 502. As an example, if the patient is currently taking birth control medication, the system may use this data as a contra-indicator that causes no hormone therapy involving progesterone or estrogen to be recommended for the patient. Similarly, if the medication history shows the patient being treated with other sex hormones as part of a menopause treatment for the patient, the system may use this data as a contra-indicator that causes no hormone therapy involving progesterone or estrogen to be recommended for the patient. As yet another example, a patient's surgical history can be used to influence how the computer system selects a recommended prescription. As an example, surgical or medical histories showing the existence of and/or treatments for certain types of cancers (e.g., breast cancer, ovarian cancer, cervical cancer, uterine cancer, and/or other cancers that are metastatic and/or known (or believed) to possess steroid-responsive cell types) may be used by the system as a contra-indicator that causes no hormone therapy involving progesterone or estrogen to be recommended for the patient.

Further still, regarding the medical or genetic information used for data 316 and 500, it should be understood that a practitioner may choose to implement the system 200 so that such data need not necessarily be the patient's direct data. A practitioner may, in some situations, deem it appropriate to use genetic or medical information from a relative of the patient (such as a first degree relative) to serve as the patient-specific data. For example, if a patient has a history of familial breast cancer, which may take the form of a 1$^{st}$ degree relative at a young age, this data may be used to represent the patient's medical information.

Figure 6A:
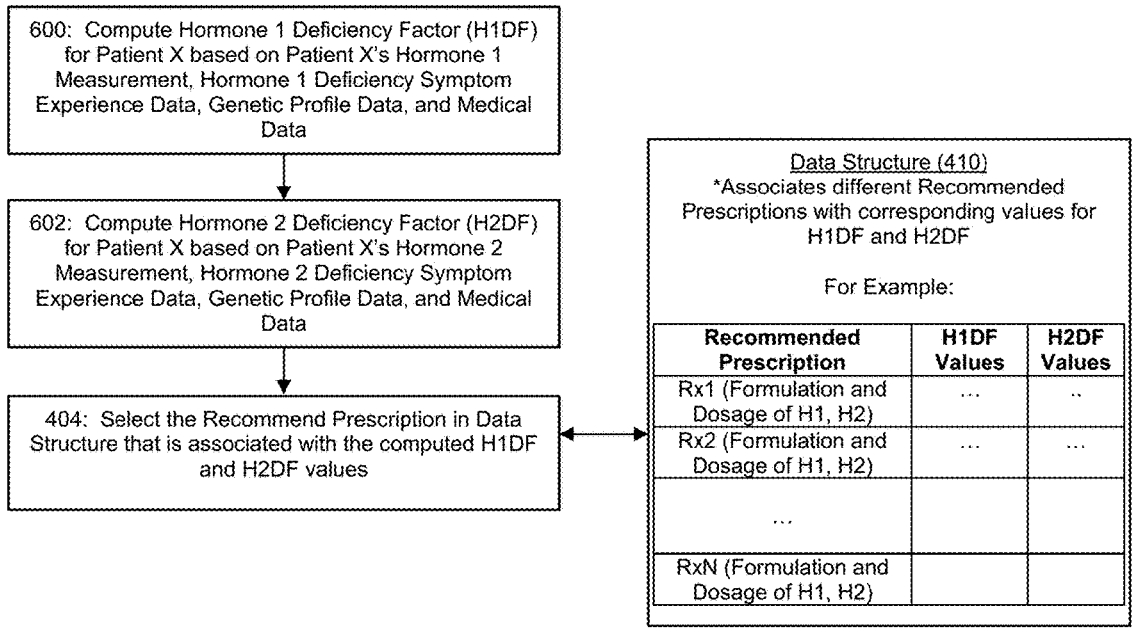
FIG. 6A depicts another example process flow for execution by a computer system to recommend hormone therapy treatment prescriptions of first and second hormones.

FIG. 6A depicts an example process flow for analysis program 502 in FIG. 5. At step 600, the processor computes H1DF for Patient X based on Patient X's H1 measurement (see data 310), H1 deficiency symptom data (see data 314), genetic profile data (see data 316), and medical data (see data 500). At step 602, the processor computes H2DF for Patient X based on Patient X's H2 measurement (see data 312), H2 deficiency symptom data (see data 314), genetic profile data (see data 316), and medical data (see data 500). Examples of techniques that can be used for computing H1DF and H2DF are discussed below. Once the H1DF and H2DF values are computed at steps 600 and 602, the processor can access the data structure 410 to look up the appropriate recommended prescription as discussed above with reference to step 404.

Figure 6B:
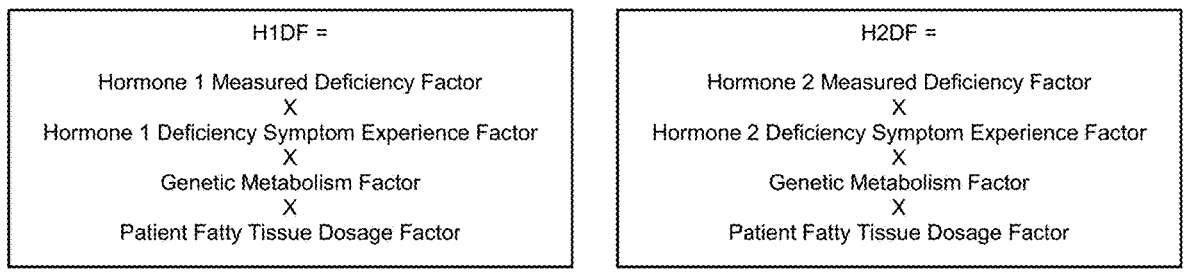
FIGS. 6B and 6C depict examples of how first and second hormone deficiency factors can be systematically computed based on a person's biochemical, symptomatic, genetic, and medical status.

FIG. 6B shows examples of functions that can be used by program 502 to compute H1DF and H2DF. H1DF can be computed as a combination of factors, including H1MDF, H1DSEF, and GMF as discussed above and further in combination with a patient fatty tissue dosage factor (FTDF). Similarly, H2DF can be computed as a combination of factors, including H2MDF, H2DSEF, and GMF as discussed above and further in combination with the FTDF.

In an example embodiment, FTDF can be computed as follows:

$$FTDF = \frac{BMI}{30} \qquad \text{Equation (13)}$$

where BMI is computed according to the formula:

$$BMI = \frac{\text{weight(kg)}}{\text{height(m)}^2} \qquad \text{Equation (14)}$$

Since height is commonly measured in centimeters, an alternate BMI calculation formula, dividing the weight in kilograms by the height in centimeters squared, and then multiplying the result by 10,000, can be used. When using English measurements, BMI can be calculated by dividing weight in pounds (lbs) by height in inches (in) squared and multiplying by a conversion factor of 703. The value for BMI can be included as part of data 500 (see FIG. 5).

Clinically, patients with a BMI over 30 generally require a higher administered hormone dose to achieve the required blood, serum, and/or tissue levels. Thus, a patient with a BMI of 35 requires a higher dose of a steroid hormone than would another patient who has a BMI of 20. Research by the inventor has established a clinical dosage baseline for a BMI of 30, above and below which the patient will require more or less hormone. Accordingly, the FTDF formula will yield the following results for the following different patients:

A 140 lb person with a height of 5'10" with a BMI of 20 would have an FTDF of 20/30, which equals 0.666.

A 170 lb person with a height of 5'10" with a BMI of 25 would have an FTDF of 25/30, which equals 0.834.

A 210 lb person with a height of 5'10" with a BMI of 30 would have an FTDF of 30/30, which equals 1.0.

A 245 lb person with a height of 5'10" with a BMI of 35 would have an FTDF of 35/30, which equals 1.16.

A 280 lb person with a height of 5'10" with a BMI of 40 would have an FTDF of 40/30, which equals 1.33.

Thus, a 280 pound, 5'10" patient with a BMI of 40 will have a suggested hormone dose roughly 1.3 times the amount of a person with a BMI of 30, and roughly 1.5 times the amount of a much thinner person with a BMI of 25. Also, as noted above, it should be understood that measurements of a patient's body fat composition characteristic other than BMI could be used to compute an FTDF value if desired by a practitioner.

Thus, FIG. 6B shows computations of H1DF and H2DF as follows:

$$H1DF = H1MDF \times H1DSEF \times GMF \times FTDF \qquad \text{Equation (15)}$$

$$H2DF = H2MDF \times H2DSEF \times GMF \times FTDF \qquad \text{Equation (16)}$$

Figure 6C:
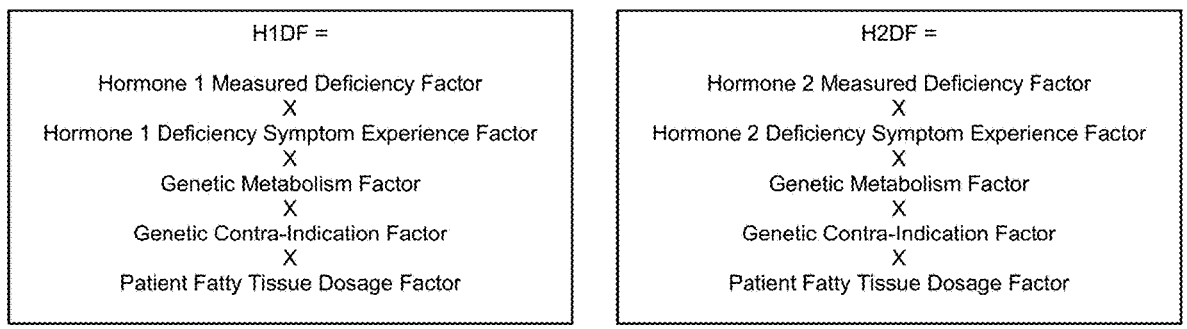

FIG. 6C shows an alternate approach to computing H1DF and H2DF for use by analysis program 502, where the H1DF and H2DF calculations also take into consideration FTDF and GCIF as discussed above. Thus, FIG. 6C shows computations of H1DF and H2DF as follows:

$$H1DF = H1MDF \times H1DSEF \times GMF \times GCIF \times FTDF \qquad \text{Equation (17)}$$

$$H2DF = H2MDF \times H2DSEF \times GMF \times GCIF \times FTDF \qquad \text{Equation (18)}$$

Based on the computed values for H1DF and H2DF, an appropriate recommended prescription can then be located and selected from data structure 410.

Accordingly, methods are thus described for providing hormone replacement therapy to a person comprising use of any of the aforementioned apparati, systems, and computer programs. In certain embodiments, such methods can comprise: (a) determining or obtaining the person's levels of a first and a second hormone; (b) determining or obtaining from the person an allelic status and/or an expression level of: (i) at least one gene which affects metabolism of the first and/or second hormones; and (ii) a gene linked to an adverse health risk for a patient if the person is treated with the first and/or second hormones; and (c) administering to the person an effective dose of a formulation comprising: (i) the first hormone, an analog thereof, a precursor thereof, and/or a metabolite thereof; and (ii) the second hormone, an analog thereof, a precursor thereof, and/or a metabolite thereof, wherein said formulation and dose are obtained by using any apparatus, computer program, and/or system provided herein. In certain embodiments, such methods can comprise administering to the person an effective dose of a formulation comprising: (i) the first hormone, an analog thereof, a precursor thereof, and/or a metabolite thereof; and (ii) the second hormone, an analog thereof, a precursor thereof, and/or a metabolite thereof, wherein said formulation and dose are obtained by using any apparatus, computer program, and/or system provided herein. In certain embodiments, such methods can comprise: (a) determining the person's levels of a first and a second hormone by obtaining a biological sample from the person and measuring the levels of the first and second hormone; (b) performing a genotyping assay to determine allelic status of: (i) at least one gene which affects metabolism of the first and/or second hormones; and (ii) a gene linked to an adverse health risk for a patient if the person is treated with the first and/or second hormones; and (c) administering to the person an effective dose of a formulation comprising: (i) the first hormone, an analog thereof, a precursor thereof, and/or a metabolite thereof; and (ii) the second hormone, an analog thereof, a precursor thereof, and/or a metabolite thereof, wherein said formulation and dose are obtained by using any apparatus, computer program, and/or system provided herein. In certain embodiments, the methods comprise determining or obtaining a deficiency factor value for a first hormone based on an analysis of (1) a measured level of the first hormone in the person, (2) symptom experience data for the person with respect to a plurality of symptoms that relate to a plurality of conditions associated with a deficiency of the first hormone in a human, and (3) genetic profile data for the person; determining or obtaining a deficiency factor value for a second hormone based on an analysis of (1) a measured level of the second hormone in the person, (2) symptom experience data for the person with respect to a plurality of symptoms that relate to a plurality of conditions associated with a deficiency of the second hormone in a human, and/or (3) genetic profile data for the person; selecting or obtaining an effective formulation and dose of the first and second hormones, analogs thereof, precursors thereof, and/or a metabolites thereof for treating the person based on the determined first and second hormone deficiency factor values; and administering to the person the selected effective formulation and dose. In any of the aforementioned contexts, terms such as "determining," "obtaining," "performing," "administering," "assaying," "genotyping," "assaying," and the like can refer to actual execution of the act or to causing the act to be executed by another. Administering can be effected by any route appropriate for the effective delivery of the formulation (e.g., topical and/or parenteral routes that include cutaneous, sub-cutaneous, intravenous, intramuscular, oral, rectal, vaginal, transdermal, and/or sublingual delivery) In certain embodiments, determination of a first and an second hormone level can be performed by assay provider which can receive and analyze a biological sample from parties that include a patient or a healthcare practitioner who obtains the sample from the patient. In certain embodiments, genotyping can be performed by a genotypic assay provider which can receive and genotype a biological sample from a patient or a healthcare practitioner who obtains the sample from the patient. Similarly, administration of the formulation can be performed by a patient or a healthcare practitioner. In certain embodiments of any of the aforementioned methods, the levels of the first and/or second hormones, the allelic status of one or more of the genes, and/or the expression levels of one or more of the genes can be obtained from a database associated with any apparatus, computer program, and/or system provided herein. In certain embodiments of any of the aforementioned methods, the first hormone is progesterone and the second hormone is estrogen. In certain embodiments of any of the aforementioned methods, the formulation further comprises a third hormone, an analog thereof, a precursor thereof, and/or a metabolite thereof. wherein the third hormone comprises testosterone. In certain embodiments, any of the aforementioned methods can further comprise determining or obtaining a body fat composition characteristic for use by the apparatus, computer program, or system. In certain embodiments, the body fat composition characteristic can be obtained from a database associated with the apparatus, computer program, or system. In certain embodiments of any of the aforementioned methods, the gene which affects metabolism of the first and/or second hormones is a member of the Cytochrome P450 (CYP) gene family. In certain embodiments, the member of the Cytochrome P450 (CYP) gene family member is CYP1A1, CYP1A2, and/or CYP1B1. the gene linked to an adverse health risk is a BRCA1 gene and/or BRCA2 gene. Expression level of genes can be measured by any effective hybridization-, amplification-, mass spectrometry, and/or nanopore based technique. Non-limiting examples of such techniques for measuring gene expression levels are disclosed in U.S. Pat. Nos. 9,624,534, 9,617,584, 9,964,538, and 10,048,245, which are each incorporated herein by reference in their entireties. In certain embodiments of any of the aforementioned methods, the second hormone is estrogen, and the formulation comprises: (i) progesterone, an analog thereof, a precursor thereof, and/or a metabolite thereof; and (ii) about 80% estradiol and about 20% estriol by weight. In certain embodiments, a high dose progesterone/low dose estrogen therapy is indicated and the formulation comprises: (i) progesterone at a concentration of about 100 mg/mL; and (ii) a composition of about 80% estradiol and about 20% estriol by weight at a concentration of about 0.4 mg/mL. In certain embodiments, an equal clinical strength progesterone/estrogen therapy is indicated and the formulation comprises: (i) progesterone at a concentration of about 80 mg/mL; and (ii) a composition of about 80% estradiol and about 20% estriol by weight at a concentration of about 2 mg/mL. In certain embodiments, a low dose progesterone/high dose estrogen therapy is indicated and the formulation comprises: (i) progesterone at a concentration of about 40 mg/mL; and (ii) a composition of about 80% estradiol and about 20% estriol by weight at a concentration of about 4 mg/mL. In certain embodiments of any of the aforementioned methods, the first hormone is progesterone, the second hormone is estradiol, and the third hormone is testosterone, and wherein the formulation comprises: (i) progesterone, an analog thereof, a precursor thereof, and/or a metabolite thereof; (ii) about 80% estradiol and about 20% estriol by weight; and (iii) dehydroepiandrosterone (DHEA). In certain embodiments, a high dose progesterone/low dose estrogen/low dose testosterone therapy is indicated and the formulation comprises: (i) progesterone at a concentration of about 100 mg/mL; (ii) a composition of about 80% estradiol and about 20% estriol by weight at a concentration of about 0.4 mg/mL; and (ii) DHEA at a concentration of about 6 mg/mL. In certain embodiments, an equivalent dose progesterone/estrogen and a low dose testosterone therapy is indicated and the formulation comprises: (i) progesterone at a concentration of about 80 mg/mL; (ii) a composition of about 80% estradiol and about 20% estriol by weight at a concentration of about 2 mg/mL; and (ii) DHEA at a concentration of about 6 mg/mL. In certain embodiments, a low dose progesterone/high dose estrogen/low dose testosterone therapy is indicated and the formulation comprises: (i) progesterone at a concentration of about 40 mg/mL; (ii) a composition of about 80% estradiol and about 20% estriol by weight at a concentration of about 4 mg/mL; and (ii) DHEA at a concentration of about 6 mg/mL. In certain embodiments, a high dose progesterone/low dose estrogen/ high dose testosterone therapy is indicated and the formulation comprises: (i) progesterone at a concentration of about 100 mg/mL; (ii) a composition of about 80% estradiol and about 20% estriol by weight at a concentration of about 0.4 mg/mL; and (ii) DHEA at a concentration of about 6 mg/mL. In certain embodiments, an equal clinical strength progesterone/estrogen and high dose testosterone therapy is indicated and the formulation comprises: (i) progesterone at a concentration of about 80 mg/mL; (ii) a composition of about 80% estradiol and about 20% estriol by weight at a concentration of about 2 mg/mL; and (ii) DHEA at a concentration of about 6 mg/mL. In certain embodiments, a low dose progesterone/high dose estrogen/high dose testosterone therapy is indicated and the formulation comprises: (i) progesterone at a concentration of about 40 mg/mL; (ii) a composition of about 80% estradiol and about 20% estriol by weight at a concentration of about 4 mg/mL; and (ii) DHEA at a concentration of about 6 mg/mL.

In certain embodiments of the aforementioned apparati, systems, computer programs and methods, the hormones of interest are thyroid hormones (e.g., thyroxine (T4) and/or triiodothyronine (T3)) and/or Thyroid-Stimulating Hormone (TSH) and the patients have thyroid hormone-associated disorders (e.g., hyperthyroidism or hypothyroidism). Symptoms associated with hypothyroidism that are tracked include fatigue, cold, constipation, weight gain, hoarseness, muscle weakness, elevated blood cholesterol, muscle aches, pain, heavier or irregular menstrual periods, thinning hair, slowed heart rate, depression, and impaired memory. Such hypothyroidism systems are addressed by thyroid hormone therapy (administration of synthetic T3, T4, analogues thereof, precursors thereof, or any combination thereof).

Symptoms associated with hyperthyroidism that are tracked include sudden weight loss (even without a decrease in appetite and food intake), rapid heart rate fatigue, increased appetite, nervousness, anxiety, irritability, tremors, changes in menstrual periods, increase heat sensitivity, changes in bowel patterns, enlarged thyroid, fatigue, muscle weakness, difficulty sleeping, and fine or brittle hair. Such hypothyroidism systems are addressed by thyroid hormone suppression therapy (e.g., administration of propylthiouracil, methimazole, and/or carbimazole).

Example Use Case: Progesterone and Estrogen

As noted above, in an example embodiment, the patient can be a woman who may be experiencing a deficiency of progesterone and/or estrogen (e.g., a patient who may be experiencing menopause symptoms). With such an example use case, H1 can be progesterone and H2 can be estrogen, in which case H1DF serves as a progesterone deficiency factor (PDF) and H2DF serves as an estrogen deficiency factor (EDF). It is expected that successful treatment of a woman's menopause symptoms arising from hormone deficiencies will need the proper amount of estrogen and progesterone (the dose) and their relative ratio within the prescription. With such an example, the data structure 410 used by the computer system 202 can be arranged as an array or grid of cells 702 as shown by FIGS. 7A-D. Each cell 702 in the array is indexed by values of EDF on the y-axis and PDF on the x-axis and can be populated with data that identifies the recommended prescription of progesterone and estrogen for those associated values of EDF and PDF. Accordingly, if the computed PDF and EDF values for a given patient fall in ranges that map to a particular cell 702, the processor can select the prescription linked to that cell 702 as the prescription to be recommended for the patient.

Figure 7A:
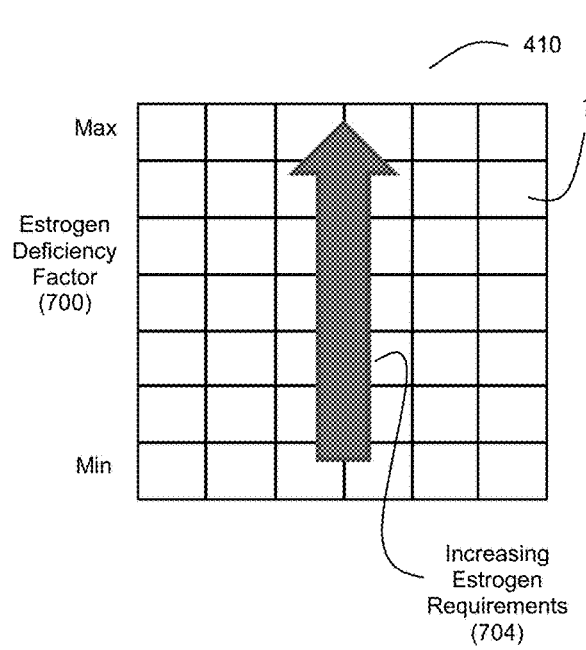
Figure 7B:
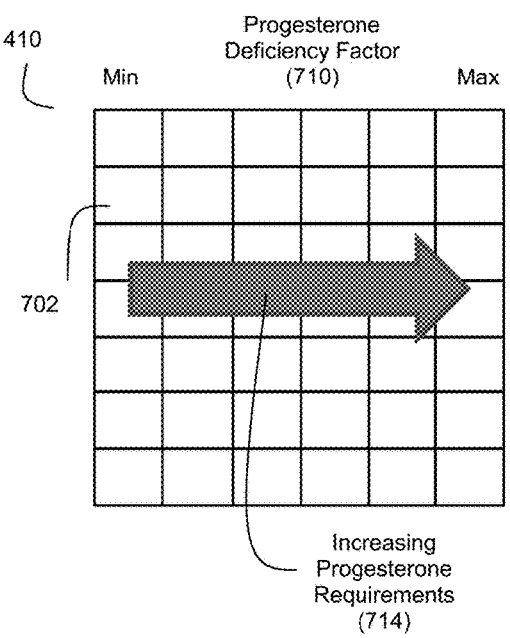
Figure 7C:
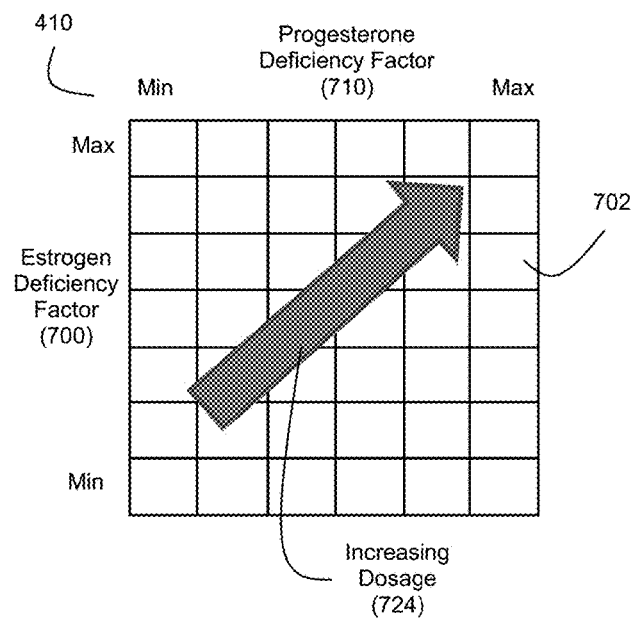

FIG. 7A shows how EDF values can be arranged on the y-axis 700 of the data structure 410 so that the minimum EDF value is at the bottom and the maximum EDF value is at the top. This means that as one moves upward in the data structure 410, this will translate into increasing estrogen requirements 704 for the prescription. FIG. 7B shows how PDF values can be arranged on the x-axis 710 of the data structure 410 so that the minimum PDF value is at the left and the maximum PDF value is at the right. This means that as one moves rightward in the data structure 410, this will translate into increasing progesterone requirements 714 for the prescription. FIG. 7C shows an overlay of FIGS. 7A and 7B, which reveals a relationship where movement in the data structure from the bottom left toward the top right translates into increasing dosage 724 for the prescription (regardless of relative mix of estrogen and progesterone in the prescription).

Figures 7D, 7E:
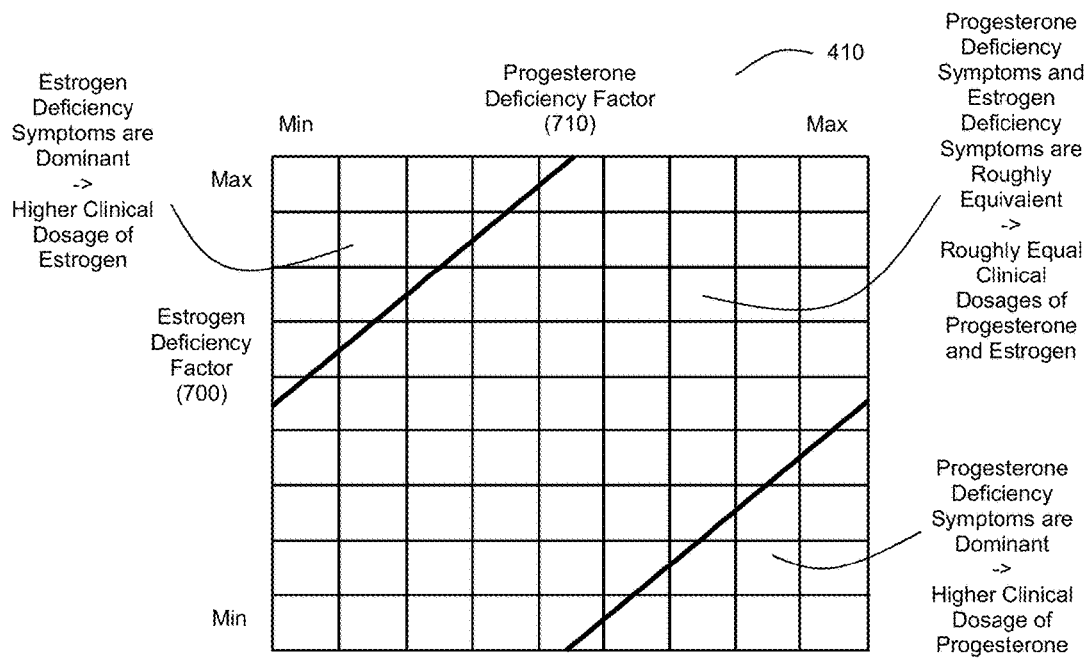

Furthermore, FIG. 7D illustrates the combination of the PDF and EDF in a grid of cells 702, each representing the requirement of estrogen and progesterone (in relative ratios) in a prescription which will adequately treat a patient with known symptoms of estrogen and progesterone deficiency and whose blood (or other body fluid) concentration (deficiency) of estrogen and progesterone is known. Within this grid, it can be seen that there is an area where estrogen requirements in the final prescription are higher than progesterone (the zone in the upper left where estrogen deficiency symptoms are dominant), an area where estrogen and progesterone requirements in the final prescription are similar (the middle zone where the progesterone deficiency symptoms and the estrogen deficiency symptoms are roughly equivalent), and an area where progesterone requirements in the final prescription are higher than estrogen (the zone in the lower right where progesterone deficiency symptoms are dominant). This translates to (1) the upper left zone having a higher clinical dosage of estrogen relative to progesterone, (2) the middle zone having roughly equal clinical dosages of estrogen and progesterone, and (3) the lower right zone having a higher clinical dosage of progesterone relative to estrogen.

Although not illustrated by FIG. 7D, the dose of the prescription increases from bottom left to upper right, as it did in FIG. 7C. Note that the amount of each hormone required to treat a patient will increase diagonally from bottom left to upper right. Those at the upper right have more symptoms and lower body fluid levels of both of the deficient hormones than those at the bottom left of the grid (where people with no symptoms and normal blood levels reside). Those at the upper right require the same relative concentrations of estrogen and progesterone in their prescription, but they require more of it (e.g., a higher dose per day) than those in the middle of the grid or towards the lower left corner of the grid.

The data structure 410 in the progesterone/estrogen example can also be scaled to have its values along the x-axis and y-axis match up with ranges of values expected for the PDF and EDF values. Toward this end, one can consider the ranges of values expected for the constituent components of PDF and EDF.

Measured Progesterone Level and Progesterone Deficiency Symptoms

In applying Equation (1) above, the goal is to compute a baseline of progesterone desired in a prescription for a peri menopausal or menopausal woman that allows for the desired clinical outcome: relief of symptoms, therapeutic levels in body fluids, without overdosing. Progesterone levels change normally during a woman's monthly cycle. This monthly variation abates once menopause has occurred and blood levels drop to largely constant low levels. When treating a patient, a lower progesterone concentration in the patient's body fluids will indicate a higher progesterone concentration in the prescribed medication. By using the inverse of the absolute concentration, Equation (1) dictates that the smaller the concentration of progesterone measured in the fluid will yield a higher concentration of progesterone in the final prescription. This calculated number reflects the actual deficiency of this hormone in the patient's blood. The normal range for progesterone in the blood of post-menopausal women is 0.1-0.6 ng/ml, and in the luteal phase of pre-menopausal women the range is 0.2-0.8 ng/ml. We can see levels as low as 0.05 ng/ml in symptomatic postmenopausal women. Thus, values for H1DF (where H1 is progesterone) can be real numbers ranging from $1/0.05=20$ at one end to $1/0.8=1.25$ at the other end (a range of 1.25–>20). It should be understood that these values are correlated to measured progesterone levels in blood samples, and these numbers will change based upon the normal range in different body fluids if samples other than blood are used for assay 210; but the final data structure 410 need not be affected by such variations. Furthermore, it should be noted that an astute physician would typically not want to prescribe progesterone to a woman whose serum progesterone is in the normal range, thus the formula for Equation (1) can be further designed to translate any value lower than 1.25 as a zero value.

In applying Equation (2) above, there are 6 symptoms commonly associated with progesterone deficiency in women (hence N=6 in Equation (2)). These symptoms are (1) anxiety, (2) crankiness, (3) painful and/or lumpy breasts, (4) unexplained weight gain, (5) insomnia, and (6) cyclical headaches. Since women experience these symptoms in a very individual way, the system allows the patient to specify severity values for these symptoms based on their own perceptions and experience. As noted above and below, a mobile application and/or web application can be provided to obtain such symptom experience data from patients. For example, the patient can be prompted for a percentage value to indicate the severity of each symptom, in which case 0% corresponds to the minimum severity and 100% corresponds to the maximum severity. These severity percentages can be translated into numbers, e.g., 0% can be recorded as 0.167 and 100% can be recorded as 1.0, and percentages between 0% and 100% can be scaled linearly between 0.167 and 1.0 as calculated to the $1/10^{th}$ (three significant digits). Accordingly, it can be seen that with such an example arrangement, the well-controlled patient with no symptoms of progesterone deficiency would have an H1DSEF of 1 (based on 6 symptoms with a symptom experience score for each of the minimum 0.167). By contrast, a patient with maximally severe symptoms of progesterone deficiency would have an H1DSEF of 6 (based on 6 symptoms with a symptom experience score for each of the maximum 1.0).

Given that Equations (4), (11), (15), and (17) each multiply H1DF by H1DSEF, it can be seen that the range for PDF needs to encompass at least 1×1.25 to 6×20; or 1.25->120, which can include a zero factor to account for patient's whose measurement levels do not indicate treatment, and thus range from 0 to 120. Furthermore, in an example embodiment as noted above where the GMF values may range from 1->1.34, this means that the upper end of the range for H1DF according to Equation (4) may reach to roughly 160. Further extensions of the upper value for the H1DF range may be desirable to accommodate the influence of FTDF under Equation (15).

Measured Estrogen Level and Estrogen Deficiency Symptoms

In applying Equation (6) above, the goal is to compute a baseline of estrogen desired in a prescription for a peri menopausal or menopausal woman that allows for the desired clinical outcome: relief of symptoms, therapeutic levels in body fluids, without overdosing. By using the inverse of the absolute concentration, Equation (1) dictates that the smaller the concentration of estrogen measured in the fluid will yield a higher concentration of estrogen in the final prescription. This calculated number reflects the actual deficiency of this hormone in the patient's blood. The normal blood levels for estrogen (estradiol) (E2) for menstruating women range from 30 to 350 pg/ml. For postmenopausal women, normal levels are typically below 30 pg/ml, and the level at which it a practitioner may find it undesirable to provide estrogen to a patient would be 30 pg/ml, and levels are not typically found below 0.1 pg/ml. Thus, values for H2DF (where H2 is estrogen) can be real numbers ranging from $1/30$=0.033 (which can be rounded to 0.04) at one end to $1/.1$=10 at the other end (a range of 0.04->10). It should be understood that these values are correlated to measured estrogen levels in blood samples, and these numbers will change based upon the normal range in different body fluids if samples other than blood are used for assay 210; but the final data structure 410 need not be affected by such variations. Furthermore, it should be noted that the formula for Equation (6) can be further designed to translate any value lower than 0.04 as a zero value.

In applying Equation (7) above, there are 5 symptoms commonly associated with estrogen deficiency in women (hence M=5 in Equation (7)). These symptoms are (1) vaginal dryness, (2) painful intercourse, (3) hot flashes, (4) night sweats, and (5) lethargy/depression. Since women experience these symptoms in a very individual way, the system allows the patient to specify severity values for these symptoms based on their own perceptions and experience. As noted above and below, a mobile application and/or web application can be provided to obtain such symptom experience data from patients. For example, the patient can be prompted for a percentage value to indicate the severity of each symptom, in which case 0% corresponds to the minimum severity and 100% corresponds to the maximum severity. These severity percentages can be translated into numbers, e.g., 0% can be recorded as 0.2 and 100% can be recorded as 1.0, and percentages between 0% and 100% can be scaled linearly between 0.2 and 1.0 as calculated to the $1/10^{th}$ (three significant digits). Accordingly, it can be seen that with such an example arrangement, the well-controlled patient with no symptoms of estrogen deficiency would have an H2DSEF of 1 (based on 5 symptoms with a symptom experience score for each of the minimum 0.2). By contrast, a patient with maximally severe symptoms of estrogen deficiency would have an H2DSEF of 5 (based on 5 symptoms with a symptom experience score for each of the maximum 1.0).

Given that Equations (8), (12), (16), and (18) each multiply H2DF by H2DSEF, it can be seen that the range for EDF needs to encompass as least 1×0.04 to 5×10; or 0.04->50, which can include a zero factor to account for patient's whose measurement levels do not indicate treatment, and thus range from 0 to 50. Furthermore, in an example embodiment as noted above where the GMF values may range from 1–22 1.34, this means that the upper end of the range for H2DF according to Equation (8) may reach to roughly 67. Further extensions of the upper value for the H2DF range may be desirable to accommodate the influence of FTDF under Equation (16).

Accordingly, in the data structure 410 of FIG. 7D, for an example embodiment, the range on the y-axis can go from 0 at the bottom to 50 at the top, and the range on the x-axis can go from 0 at the far left to 120 at the far right. Furthermore, a practitioner can divide this 50×120 grid space into a number of cells 702 where each cell corresponds to some range of values with respect to EDF and PDF. With this example, if the values for GMF and/or FTDF cause the computed H1DF and/or H2DF values to exceed the grid range, the system can operate to select the maximal H1DF and/or H2DF value as applicable. However, in other example embodiments, the data structure 410 may include y-axis and x-axis ranges that go beyond 50 and 120 respectively so that the upward adjustments caused by GMF and/or FTDF can be directly encoded in the cells 702 of the grid.

Formula and Dose of Estrogen and Progesterone Within a Prescription Grid Data Structure Continuing with the example of FIG. 7D, the grid data structure for PDF and EDF can have 50 rows (0 to 50) and 60 columns (0 to 120, by two's), which correspond to the EDF and PDF as described above. Each cell 702 can be populated by a three digit code (E, P, D) corresponding to its estrogen number (Y axis), progesterone number (x axis) and dose being established from bottom left to upper right. The x (P) and y (E) coordinates of this grid will dictate the final concentration of estrogen and progesterone (respectively) in the final prescription (the formula of the drugs, in mg/ml), with the D component corresponding to the dose prescribed (how much of the formula, and how often) which was established previously as increasing from lower left to upper right (and will be modified subsequently).

The P/E Ratio and the Recognition of "Estrogen Dominance" Menopause Symptoms The ratio of measured (blood/serum/saliva/urine) progesterone to estrogen is helpful in clinical practice when providing an appropriate hormone replacement therapy prescription. These situations give rise to clinical syndromes known as "Estrogen Symptom Dominance" and "Progesterone Symptom Dominance" and are characterized by symptoms typical of deficiencies of one or the other hormone but it is more complex than that with their relative ratios being of clinical significance and not necessarily the true levels. Thus, the P/E Ratio can be a component of the treatment system 200. By the very nature of the table comparing the EDF (incorporating both symptoms of estrogen deficiency and measured hormone levels) and the PDF (incorporating symptoms and hormone levels), the entire relationship (the grid) represents a ratio of progesterone to estrogen symptoms and ultimately requirements within the ultimate prescription. As shown by FIG. 7D, the areas of estrogen symptom dominance and progesterone symptom dominance are readily contained and represented within this methodology.

High P/E Ratio

A high P/E ratio occurs when estrogen is low relative to progesterone. This describes the classic situation of Estrogen Symptom Dominance and illustrated in the top left corner of FIG. 7D as noted above. Here the symptoms of estrogen deficiency (and EDF) are high and the symptoms of progesterone deficiency (and PDF) are low. Within the methodology here, increasing estrogen (with or without decreasing progesterone) in the prescribed hormone therapy is appropriate.

Low P/E Ratio

A low P/E ratio occurs when measured serum (blood, saliva) progesterone is low relative to estrogen. This is progesterone symptom dominance and is represented in the bottom right of FIG. 7D as noted above. This aspect is incorporated into our methodology and is associated with higher doses of progesterone in the final prescription.

Theoretically, the estrogen and progesterone example discussed herein provides for at least 6,000 different and unique prescription formulas for estrogen and progesterone (50×120). This may be appropriate where the prescriptions are filled by an automated machine which can mix the drug as prescribed; however it becomes cumbersome if the prescriptions are filled by hand. Moreover, supporting such a huge number of possible variations in formulations and dosage also makes high volume batch production impractical. However, the ability to mass produce formulations of progesterone/estrogen treatments would be highly beneficial in that it could help decrease costs to patients and provide other benefits such as increased sterility and dose-to-dose consistency in potency and makeup.

Further still, the data structure 410 described herein comprised of an array of cells 702 indexed by H1DF and H2DF values allows for the data structure 410 to be readily scaled up or down to more or fewer number of available prescription formulas. For example, a table with 6,000 unique cells 702 could be readily reduced to 100 unique cells 702 by combining every 5 rows of the table into a single row and by combining every 12 columns of the table into a single column, thereby yielding a 10×10 table. Managing 100 unique formulations/dosages of H1 and H2 may be more manageable for practitioners. Moreover, because of the spatial and linear relationships along the two axes, the scale can be readily reduced (or increased) based on the level of granularity in recommendations that a practitioner desires for the system. That is, data structure 410 as shown by FIG. 7D allows for the grouping of women with similar symptoms and hormone levels as necessary to bring the final number of choices for the ultimate hormone prescription down to a reasonable number with the goal that they may be treated to the desired clinical endpoints (symptomatic relief and bone protection) at the lowest possible dose, achieved via the fewest possible formulations.

Formulations of Estrogen and Progesterone

Based on clinical testing and the review of approximately 10,000 prescriptions written by over 1000 physicians for bioidentical hormone replacement therapy, the inventor has concluded that only 3 relative concentrations of estrogen and progesterone are needed to successfully treat >95% of menopausal (and perimenopausal) women to the desired clinical endpoint of (1) lowest possible dose to achieve (2) symptomatic relief, and (3) long-term bone protection. As established by the data structure 410 of FIG. 7D, the three formulations of estrogen and progesterone will have (1) one where estrogen is provided in higher clinical concentrations relative to progesterone, (2) one where progesterone is provided in higher clinical concentrations relative to estrogen, and (3) one where the two are provided in relative equal clinical strengths. FIG. 7E shows a table that identifies examples of these 3 formulations. It should be understood that FIG. 7E is merely an example; some practitioners may choose to employ a greater number of formulations, and or formulations with different mixes of clinical strengths for estrogen and progesterone.

In FIG. 7E, Formula 1 is progesterone-predominant (progesterone is provided in a higher clinical concentration relative to estrogen). Formula 2 provides doses of estrogen and progesterone in equal clinical strengths. Formula 3 is estrogen-predominant (estrogen is provided in a higher clinical concentration than progesterone).

FIG. 7F shows the formulations of FIG. 7E being mapped into cells 702 of data structure 410. The prescriptions in each cell 702 are identified by a pair of numbers indicating Formula Number and Dosage; hence a value of (3,2) translates to Formula 3 with a dosage of 2 units. The units of dosage can vary depending on the modes of administration chosen by a practitioner. For example, hormone treatments are often administered as topical creams that are applied to a skin surface, where the cream embodies the prescribes formulation of progesterone and estrogen.

Figure 11:
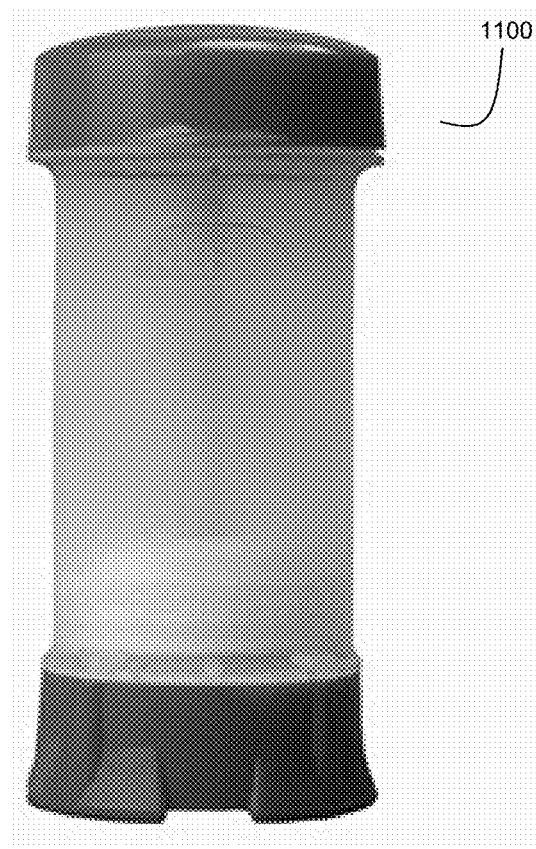
FIG. 11 depicts an example dispensing system for a hormone therapy treatment prescription.

Dispensers such as the dispenser 1100 shown by FIG. 11 can be used to dispense such cream to the patient in the proper amount for each dose. FIG. 11 shows a Topi-CLICK drug delivery system that can be suitable for use to dispense prescribed hormone therapy treatments in example embodiments. The Topi-CLICK system is a cream dispensing system available from DoseLogix, Inc. of Woodstock, Ga.

For example, the dispenser 1100 can be arranged to dispense a defined amount of cream in response to a patient action on the dispenser (e.g., often referred to as "clicks"). Thus, each click can cause the dispenser to dispense an amount of cream such as in 0.5 ml aliquots. In such a situation, dosage units of 1 may correspond to 1 click of cream per day, dosage units of 2 may correspond to 2 clicks of cream per day, dosage units of 3 may correspond to 3 clicks of cream per day, and dosage units of 4 may correspond to 4 clicks of cream per day. However, these are merely examples and other dose units can be employed by a practitioner if desired.

Forms of Estrogen Used in Clinical Medicine

As noted above, estrogen may be prescribed in any of a number of forms. For example, Biest is a common form of estrogen used with hormone therapy treatment. Biest is a combination of estradiol (E2) and estriol (E3). Estradiol is a fairly strong form of estrogen with strong activation of estrogen receptors on target cells. Estriol has a longer half-life and activates target receptors to a much lesser degree; thus it "buffers" and balances the stronger, more "aggressive" estradiol.

Estradiol treatment by itself can cause breast tenderness, further exacerbate fibrocystic breast disease, weight gain in the stomach, increase risk for uterine cancers by increasing the endometrial proliferation/lining and moodiness. Estriol treatment alone is too weak for most women's menopausal symptoms. Which is why by treating with Biest, the estriol can reduce the powerful effects of estradiol but still achieve successful menopausal relief and anti-aging. The most common form of Biest used world-wide is an 80:20 ratio; with estriol encompassing 80% of the dose and estradiol 20%. Example embodiments described herein will employ Biest as the active form of estrogen in the prescription formulations. However, it should be understood that these are merely examples; and other practitioners may find it more desirable to use other forms of estrogen in the prescription formulations.

User Interface Applications

Figure 8A:
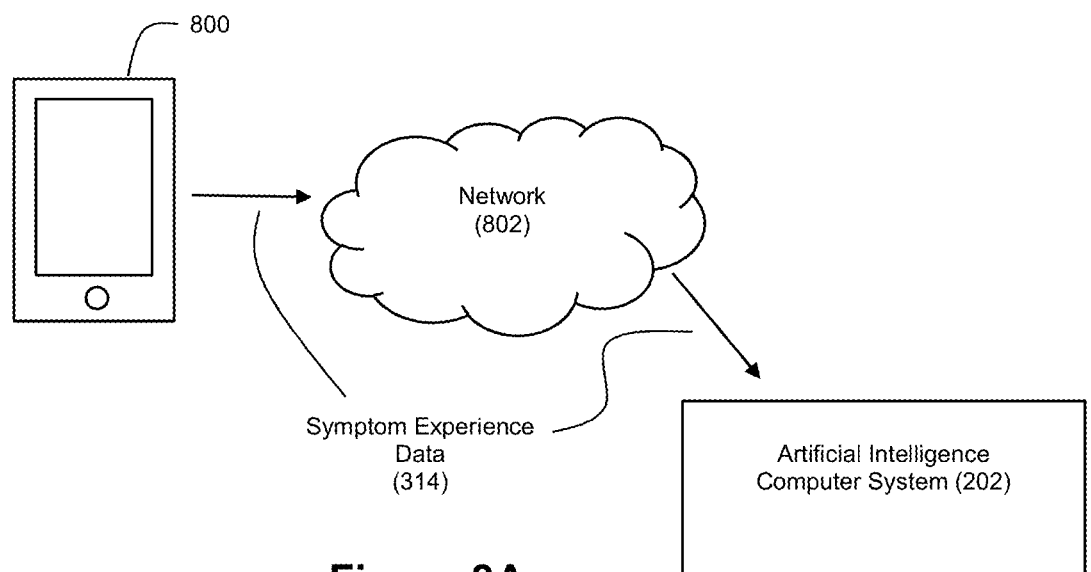
FIG. 8A depicts an example system where a mobile application can be used to collect symptom experience data from patients.

As noted above, the system 200 can include applications such as a mobile application and/or web application that interface with various users of the system. For example, FIG. 8A depicts an example system where a mobile application can be used to collect symptom experience data 314 from patients. A mobile application can be installed and executed from a mobile computing device 800 such as a smart phone or tablet computer. The mobile computing device 800 can communicate with the AI computer system 202 via a network 802. The network 802 can be any suitable network or networks for communicating data between the mobile computing device 800 and computer system 202 (e.g., a wireless network, a cellular data network, and/or the Internet). The mobile application executed by mobile computing device 800 can cause one or more user interfaces to be presented on a display screen of the mobile computing device 800. Through such user interface(s), the patient can provide his or her symptom experience data 314, and the mobile computing device 800 can communicate such symptom experience data 314 to the computer system 202 via network 802.

Figure 8B:
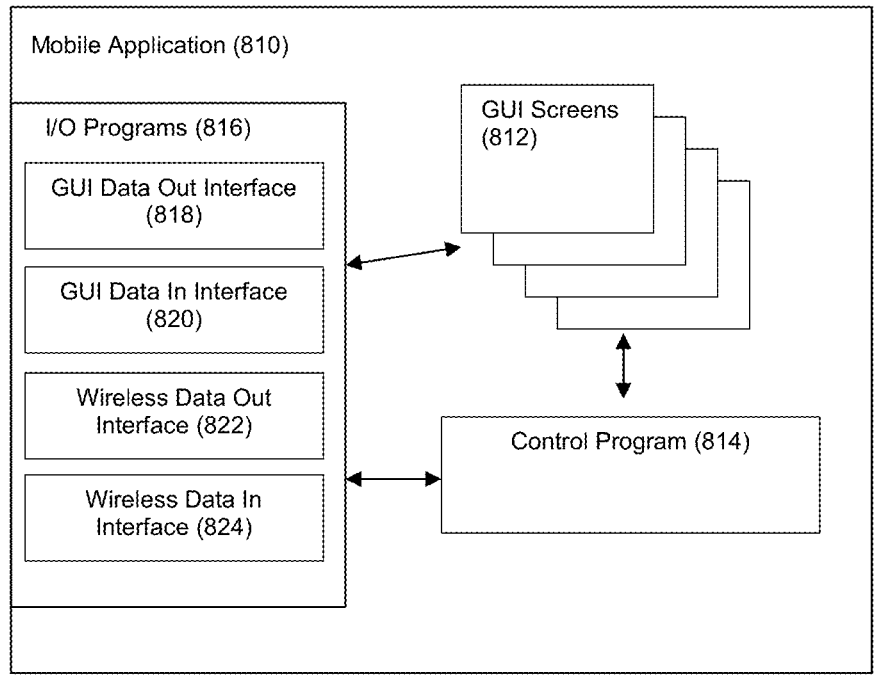
FIG. 8B depicts an example mobile application for use with FIG. 8A.

FIG. 8B depicts an example mobile application 810 for use with FIG. 8A. The mobile application 810 can include a plurality of graphical user interface (GUI) screens 812 through which the patient can interact with the mobile application 810. A control program 814 can then interact with the GUI screens 812 and various native features of the mobile computing device via I/O programs 816. For example, the I/O programs 810 can include a GUI data out interface 818 which interfaces the GUI screens 812 with display rendering capabilities of the mobile computing device 800 so that the GUI screens 812 can be presented to the patient via the display screen of the mobile computing device 800. The I/O programs 810 can also include a GUI data in interface 820 which interfaces the GUI screens 812 with the data input (e.g., touchscreen input) capabilities of the mobile computing device 800 so that the mobile application 810 can collect any input from the patient via the GUI screens 812. The I/O programs 810 can also include a wireless data out interface 822 which interfaces the mobile application 810 with the wireless data (e.g., WiFi or cellular data) communication capabilities of the mobile computing device 800 so that the mobile application 810 can send the symptom experience data 314 to the computer system 202. Further still, the I/O programs 810 can also include a wireless data in interface 824 which interfaces the mobile application 810 with the wireless data (e.g., WiFi or cellular data) communication capabilities of the mobile computing device 800 so that the mobile application 810 can receive wireless data communications from remote computer systems such as computer system 202.

FIGS. 8C and 8D depict example user interfaces for the mobile application 810. FIG. 8C shows an example GUI 850 that is designed to solicit and receive inputs from the patient that quantify hormone deficiency symptoms (e.g., symptoms of a progesterone deficiency in this example). As noted above, progesterone deficiency symptoms can include (1) anxiety, (2) crankiness, (3) pain or lumpiness in breasts, (4) unexplained weight gain, (5) insomnia, and (6) cyclical headaches. The GUI 850 can include user input mechanisms such as slider bars 852 corresponding to each symptom through which the user quantifies a severity of each symptom. In this example, the severity is expressed on a percentage scale; but it should be understood that other scales could be used (e.g., a score between 1 and 10, a score between 1 and 100, a text score (low, low/medium, medium, medium/high, high), etc.). Also, the user input mechanism need not be slider bars 852 and could be other mechanisms if desired by a practitioner (e.g., radio buttons, data entry fields, etc.). The GUI 850 can also include a "next" button 854 or the like that is user-selectable to submit the entered symptom experience data 314 as well as a "clear" button 856 or the like that is user-selectable to clear any previously-entered progesterone deficiency symptom experience data 314.

FIG. 8D shows another example GUI 860 that is designed to solicit and receive inputs from the patient that quantify additional hormone deficiency symptoms (e.g., symptoms of an estrogen deficiency in this example). The GUI screen 860 may be reached after user selection of the "next" button 854 from FIG. 8C; although it should be understood that a practitioner could switch the navigational order of GUIs 850 and 860 if desired or even combine them into a single GUI. Further still, a practitioner may choose to further subdivide the various prompts about different progesterone and estrogen deficiency symptoms across more than 2 GUIs if desired. As noted above, estrogen deficiency symptoms can include (1) vaginal dryness, (2) painful intercourse, (3) hot flashes, (4) night sweats, and (5) lethargy/depression. The GUI 860 can include user input mechanisms such as slider bars 862 corresponding to each symptom through which the user quantifies a severity of each symptom. In this example, the severity is expressed on a percentage scale as with GUI 850; but as noted above other scales could be used if desired by a practitioner. Also, the user input mechanism need not be slider bars 852 as noted above. The GUI 860 can also include a "submit" button 864 or the like that is user-selectable to submit the entered symptom experience data 314 as well as a "clear" button 866 or the like that is user-selectable to clear any previously-entered estrogen deficiency symptom experience data 314 and a "back" button 868 or the like that is user-selectable to navigate back to GUI 850.

It should be understood that GUIs 850 and 860 are examples only, and the mobile application 810 may include additional GUIs if desired by a practitioner. For example, the mobile application 810 may include a "home" GUI that provides navigation to GUIs 850 and/or 860. Other GUIs available via mobile application 810 may provide the user with history data about their symptoms and prescriptions if applicable.

Further still, while FIGS. 8A-8D describe an example embodiment where a mobile application is used to collect symptom experience data from patients, the system can also employ a web application for this purpose. In such a case, the computer system 202 can make a website available for access by users via their own computers (e.g., laptops, desktops, etc.). Website pages can then provide the GUIs similar to those shown above for FIGS. 8C and 8D to collect symptom experience data from patients.

Also, while FIGS. 8C and 8D show GUIs for a mobile application 810 for use by patients, it should also be understood that the system can also include mobile or web applications for use by other participants in system 200.

Figure 8F:
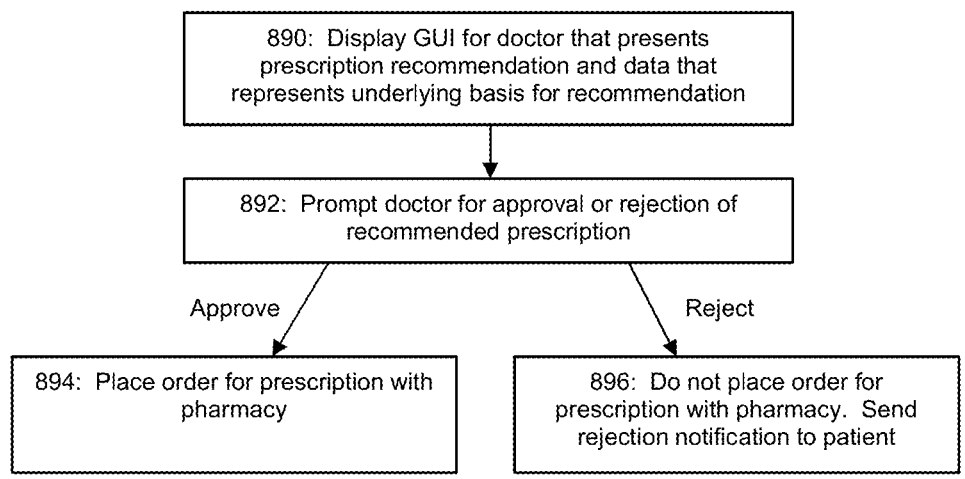
FIG. 8F depicts an example process flow for the computer system to take actions in response to doctor input via the user interface of FIG. 8E.

For example, doctors 206 may also have a mobile or web application that they can access to review the prescription recommendations generated by the system 200 for their patients. Such a mobile or web application can include a user interface that identifies a patient, the recommended prescription for that patient, and audit trail data that shows how the system arrives at the recommended prescription. An example of such a user interface is shown by FIG. 8E (see GUI 870). FIG. 8F shows an example process flow with respect to FIG. 8E. At step 890 of FIG. 8F, GUI 870 is presented on a screen of a computer used by the doctor. This GUI 870 can be a GUI produced by a mobile app executing on a doctor's mobile computing device (e.g., smart phone or tablet computer), or the GUI 870 can be a web page that is accessed from a website or other web application hosted by computer system 202. GUI 870 includes a section 872 that identifies the subject patient (which may include any amount of desired information that identifies the subject patient). GUI 870 also includes a section 874 that identifies the patient's current biochemical status as derived from assay 210. Section 874 may present not only the measured hormone levels but also a date for the measurement and a source type for the measurement (e.g., blood, saliva, etc.). GUI 870 also includes a section 876 that identifies the patient's current symptomatic status as derived from patient inputs via GUI screens 850 and 860. This information may present the overall scores for H1DSEF and H2DSEF. However, section 876 may also present additional information such as the individual symptom severities if desired by a practitioner. GUI 870 also includes a section 878 that identifies the patient's genetic status, which may include identifications of whether any genes that have an impact on treatment options under the system are present in the patient.

At step 892 of FIG. 8F, the system prompts the doctor for approval or rejection of the recommended prescription. This can be accomplished via sections 880 and buttons 882, 884 of the GUI 870. Section 880 of GUI 870 displays the recommended hormone therapy treatment prescription. For ease of illustration, section 880 identifies the recommended prescription in shorthand; however, it should be understood that section 880 may provide a more detailed, itemized description of the prescription if desired by a practitioner. GUI 870 permits the doctor to consider whether the recommended hormone therapy treatment prescription in section 880 in the context of the underlying data as presented via sections 874, 876, and 878. If the doctor agrees with the recommendation in 880, the doctor can select the "approve" button 882. Selection of the "approve" button can cause the computer system to place an order for the subject prescription with a pharmacy (step 894 of FIG. 8F). The subject pharmacy can be identified based on a data structure that associates the subject patient with a particular pharmacy or through some other mechanism. If the doctor disagrees with the recommendation in 880, the doctor can select the "reject" button 884, in which case no prescription order is placed (step 896 of FIG. 8F). As part of step 896, the system may also notify the patient about the rejection. Accordingly, it can be seen that GUI 870 provides doctors with actionable intelligence for efficiently prescribing patients with effective hormone therapy treatments.

Also, while the example of FIG. 8E shows a single GUI 870 providing a large amount of information to the doctor about the patient and recommended prescription, it should be understood that a practitioner may choose to include additional or less information about the patient if desired.

For example, the GUI 870 may include only the computed H1DF and H2DF values in combination with section 880 and buttons 882, 884.

In yet another example, the GUI 870 can present the recommendation in the context of a visual depiction of the grid data structure 410 where the visual depiction also shows which cell the H1DF and H2DF values indicate, thereby identifying the recommended prescription.

In another example, the GUI 870 can also include additional sections that present patient medical information such as BMI, medical history, and/or medication history.

In yet another example, the GUI 870 could also include history information for the patient's biochemical and/or symptomatic status. For example, section 874 could include plots of the patient's progesterone and estrogen measurements over time, such as showing measured hormone levels on a y-axis and time on an x-axis). Such plots could also include graphical features that show the normal levels for those hormones (for example, via a horizontal line or bar showing the normal ranges for such hormone levels). Such a plot can allow a doctor to quickly and intuitively understand if the patient's measured hormone levels are improving or regressing over time. As another example, section 876 could include plots of the patient's progesterone and estrogen deficiency symptom experience data over time, such as showing the computed H1DSEF and H2DSEF scores on a y-axis and time on an x-axis). Such a plot can allow a doctor to quickly and intuitively understand if the patient's symptoms are improving or regressing over time, thereby allowing the doctor to assess whether a given treatment may be working or not. Also, such plots can be provided at the individual symptom level if desired by a practitioner.

Further still, a practitioner may choose to spread the subject information over multiple GUIs rather than consolidating on a single GUI.

Also, GUI 870 can provide the doctor with a mechanism for adjusting the prescription if desirable. For example, the prescription could be displayed on the corresponding cell of a visually-presented grid data structure 410 that was indicated by the H1DF and H2DF scores. If the doctor decides that a heavier concentration of progesterone and/or estrogen (and/or heavier overall dosage) is desired, the doctor could select a nearby cell on the grid data structure 410 to locate a prescription with desirable characteristics, as discussed above and below.

Furthermore, in an alternate example embodiment, the computer system 202 may not necessarily recommend a prescription to the doctor 206 via the doctor-facing mobile or web application. Instead, the doctor 206 could be provided with a chart or index or the like that corresponds to a visual depiction of data structure 410 (mapping different hormone therapy prescriptions to particular H1DF, H2DF value pairs), and the GUI presented to the doctor can show the patient's computed H1DF and H2DF values (optionally with supporting audit trail data as well). The doctor can then consult the chart/index to identify the appropriate prescription for the patient in view of the computed H1DF and H2DF values. The chart/index could be provided to doctors 206 offline (e.g., as a paper chart/index) for reference by the doctors 206 when using the doctor-facing application; or the chart/index could be electronically presented to doctors 206 via one or more GUIs of the doctor-facing application.

As yet another example, pharmacies 208 may also have a mobile or web application that they can access to receive and review prescription orders from computer system 202. Similarly, testing companies that process the assays 210 and 212 could also access a mobile or web application for communicating the patient's hormone measurements and genetic profile data to the computer system 202. Through network communications via a mobile or web application, computers operated by testing companies can transfer data that represents the patient's hormone measurements and genetic profile via electronic file system exchanges. However, it should be understood that other techniques for data transfer could be employed, including manual data entry by an operator of computer system 202.

Learning and Feedback

Figure 9:
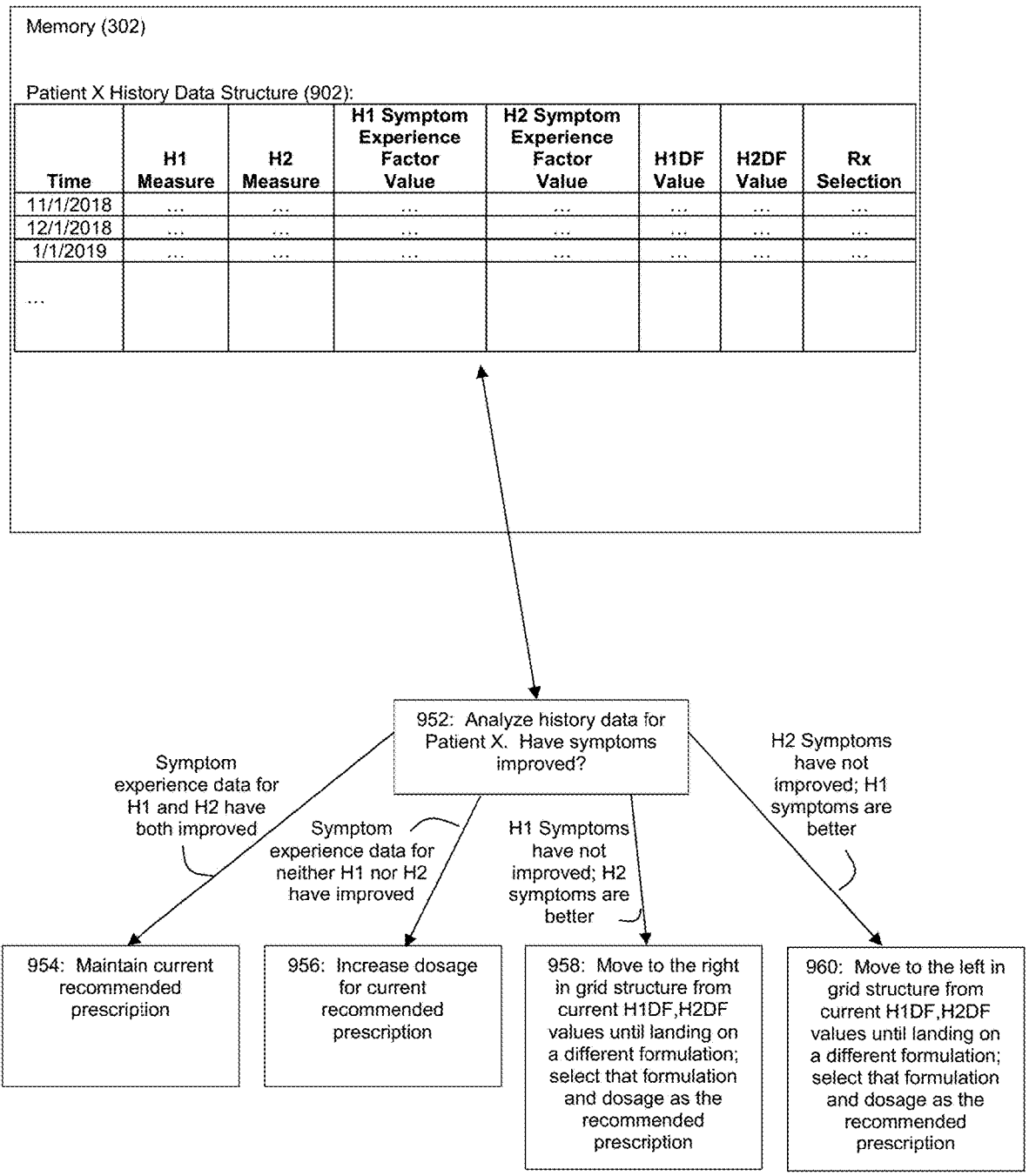
FIG. 9 depicts an example process flow where feedback is used to track symptoms over time and make adjustments to prescription recommendations.

Computer system 202 can also provide powerful learning and feedback capabilities so that the prescriptions it recommends can improve over time. Such learning/feedback can be implemented at an individual patent level and/or an aggregated multi-patient level. To support such operations, the memory 302 within computer system 202 can store history data about the patients who are using the system 200. This history data can track the patient's symptoms, hormone measurements, and prescriptions over time (along with any other relevant medical information about the patient). FIG. 9 shows an example of a history data structure 902 that can be stored in memory 302 in association with a patient (e.g., Patient X) to provide such history tracking. The history data structure 902 can include entries that are tagged by time, where each entry identifies various items of data about the subject patient for that subject time. Such data can include the H1 measurement, the H2 measurement, the H1 deficiency symptom experience value(s) (the aggregated H1DSEF value and/or the component values at the individual symptom level), the H2 deficiency symptom experience value(s) (the aggregated H2DSEF value and/or the component values at the individual symptom level), the H1DF value, the H2DF value, and the prescription selection for the relevant time.

Analysis program 304 can then use this history data to help guide and influence future prescription selections for the subject patient. FIG. 9 shows an example process flow for this. At step 952, the processor analyzes the history data in history data structure 902 for the subject patient. In an example embodiment, this analysis can be focused on the patient's symptom data. For example, at step 952, the processor can compare current symptom experience data with past symptom experience data. If this comparison reveals that the patient's symptom experiences have improved (for symptoms of both H1 and H2 deficiencies), then the processor can conclude that the patient's prescription need not be modified (step 954). However, if this comparison reveals that the patient's symptoms have not improved, the processor can adjust the prescription selection accordingly.

For example, if the comparison at step 952 shows that the symptom experience data for neither H1 nor H2 have improved (either they have stayed the same or gotten worse since the last check), then the processor can choose to increase the dosage for the current prescription formulation (step 956). That is, keep the same clinical mix of H1 and H2 in the prescription, but increase the dosage.

If the comparison at step 952 shows that the symptom experience data for H1 has not improved (either it has stayed the same or gotten worse since the last check) while the symptom experience data for H2 has improved, then the processor can choose to alter the formulation mix for the prescription so that there is more H1 in the mix relative to the previous prescription (step 958). With reference to the data structure 410 as shown by FIGS. 7D and 7F, this may involve moving to the right in the grid while staying in the same row until landing on the cell with the next different formulation. The prescription corresponding to that cell can then be recommended by the processor.

If the comparison at step 952 shows that the symptom experience data for H2 has not improved (either it has stayed the same or gotten worse since the last check) while the symptom experience data for H1 has improved, then the processor can choose to alter the formulation mix for the prescription so that there is more H2 in the mix relative to the previous prescription (step 960). With reference to the data structure 410 as shown by FIGS. 7D and 7F, this may involve moving to the left in the grid while staying in the same row until landing on the cell with the next different formulation. The prescription corresponding to that cell can then be recommended by the processor.

It should be understood that a practitioner can choose to implement such a learning/feedback model in any of number of ways. For example, the learning/feedback could be applied for each new prescription and only perform a comparison with symptom data from the previous prescription. In another example, the system could combine the symptom data from several prior prescriptions to establish a symptom trend over a longer time duration and then use such an aggregated symptom trend as the point of comparison rather than just the symptom data from the time immediately prior. Also, given that the H1DSEF and H2DSEF values operate to quantify the symptom data for H1 and H2 deficiencies in an aggregated manner for each of the H1 deficiency symptoms and the H2 deficiency symptoms, the comparison at step 952 can be between current/past H1DSEF values and current/past H2DSEF values. However, a practitioner could also implement such comparisons at a more granular individual symptom level if desired. Also, it should be understood that a practitioner can design the system to analyze more than symptom data at step 952. For example, the processor can also compare how the hormone measurements have changed over time and use that to influence its decision-making as to whether adjustments in the prescription are desirable. For example, if the system detects that a patient has some symptom relief and measured hormone levels that are in a medium therapeutic range, the system can choose to recommend a decrease in dosage for the prescription. Also, rather than automatically adjusting the recommended prescription, the system could instead generate a notification to the doctor 206 regarding which if any of the hormone deficiency symptoms remain problematic for the patient; and the doctor can then use that information to make a decision about increasing dosage and/or changing formulations.

In another example embodiment, the feedback/learning can operate at a higher level of aggregation across history data for multiple patients. Thus, memory 302 can store a database of history data for multiple patients, and the processor can analyze such cumulative data to assess whether any of the hormone therapy formulations and/or any of the assignments of prescriptions to grid cells 702 should be adjusted. For example, if a large percentage of patients taking a particular formulation are subsequently changed to a different formulation, the system can detect this condition in the history data, and then implement a corrective action. For example, if the history data for a number of patients in excess of some defined threshold shows that a particular prescription at a given cell 702 is consistently needing to be changed to a different prescription in order to achieve symptom relief, then the system can choose to change the prescription assigned to that grid cell 702 to reflect the prescription to which the patients are often being changed. Also, if the history data shows a more general problem for a particular formulation (e.g., Formula X) across multiple cells 702, the system may detect this and recommend that Formula X is not particularly effective and should itself be adjusted.

In another example embodiment, the history data can be analyzed to optimize the formulae used by the analysis program to compute H1DF and H2DF. For example, data analysis might reveal that better results can be achieved if different weights were assigned to different symptoms in Equations (2) and (7). Similarly, the weights assigned to the components of the genetic metabolism factor may also be adjusted if the history data shows that these could be further optimized. For example, it may be found that patients taking hormones via the cutaneous skin route do not require as much emphasis on liver breakdown enzymes (e.g., CYP450 enzymes) and this the increase in dose assigned by the GMF value due to genetic CP450 variants may be over-valued by the system's analysis, which may result in higher measured hormone levels in those patients that are detected by follow-up assays 210. In such a situations, a practitioner may choose to modify the weights in the GMF calculation for patients who are taking hormones via the cutaneous skin route. Further still, data analysis might reveal that better results can be achieved if different weights and/or scalars were assigned to different component factors in Equations (4), (8), (11), (12), (15), (16), (17), and (18). For example, analysis of history data might reveal that better results would be achieved if the weight of the symptom data took precedence of the weight of the hormone measurement data in the H1DF and H2DF calculations.

Example Use Case: Progesterone, Estrogen, and Testosterone

While the examples discussed above involved hormone therapy treatment with two hormones, it should be understood that treatments using the techniques described herein could also be extended to additional numbers of hormones, such as a third hormone in the formulation. With respect to the menopause-related example above involving treatment with progesterone and estrogen, an additional example embodiment could also include testosterone as a component of the hormone therapy treatment. Testosterone is well known as a "male" hormone, but women have testosterone in their blood as well. In fact, testosterone levels in women decrease dramatically after menopause like the classic female hormones estrogen and progesterone. The normal level of testosterone in adult females is 15 to 70 ng/ml; and doctors may choose not to prescribe testosterone (or a testosterone analog or metabolite) to women with testosterone levels above 25 ng/ml. And, just as estrogen and progesterone have symptoms associated with low levels (deficiencies), low levels of testosterone in women can also be manifested in symptoms such as decreased libido, chronic fatigue, painful intercourse, dry skin, and loss of muscle tone in arms and legs. As explained below, the technology described herein can also be used to take into account any testosterone amounts that may be desirable to include in hormone therapy treatment prescriptions.

Figure 10A:
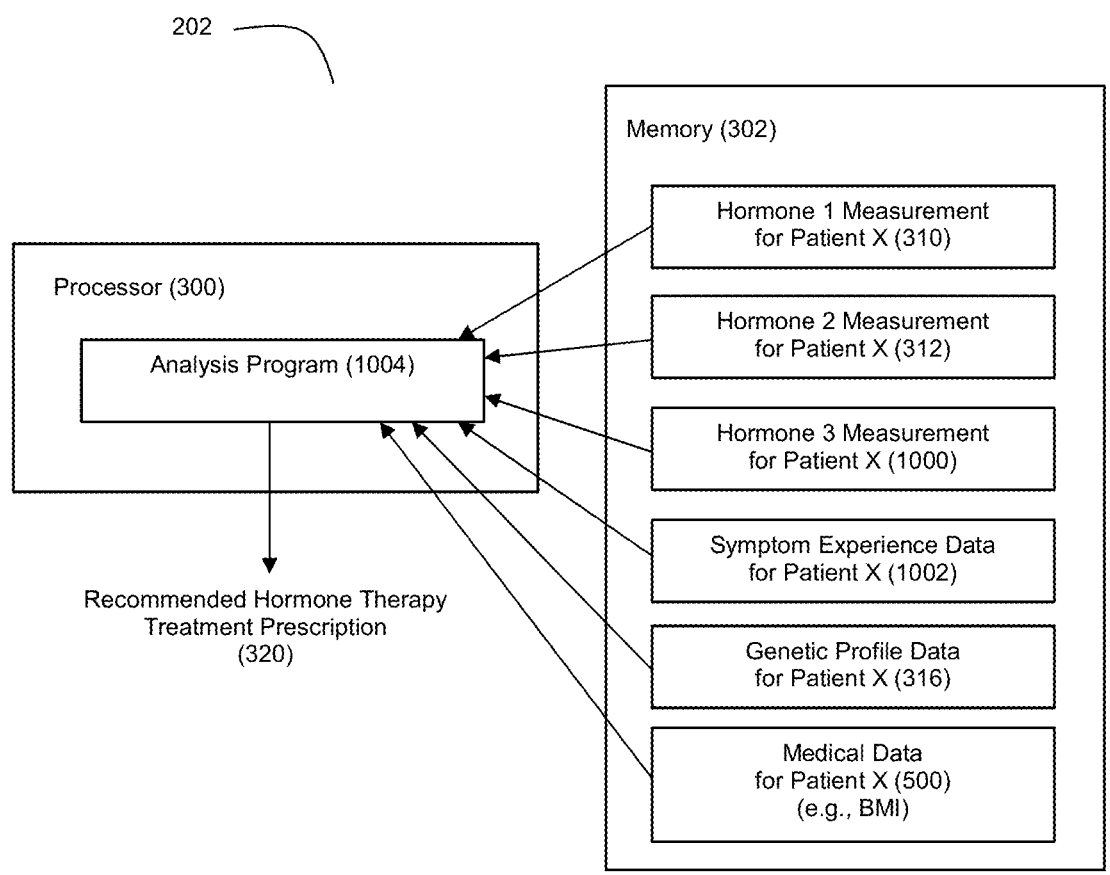
FIG. 10A depicts an example computer system for use with the treatment system of FIG. 2 to recommend a hormone therapy treatment prescription of first, second, and third hormones.

FIG. 10A shows an example computer system 202 that can generate recommended hormone therapy prescriptions for mixes of 3 hormones, such as progesterone, estrogen, and testosterone. The analysis program 1004 executed by processor 300 can operate in a similar fashion as the analysis programs described in connection with FIGS. 3 and 5; but it can also take into consideration measurement data 1000 for the third hormone (H3) and where the symptom experience data 1002 includes not just symptom experience data for deficiencies of H1 and H2 but also symptom experience data for H3 deficiencies.

Figures 10B, 10C:
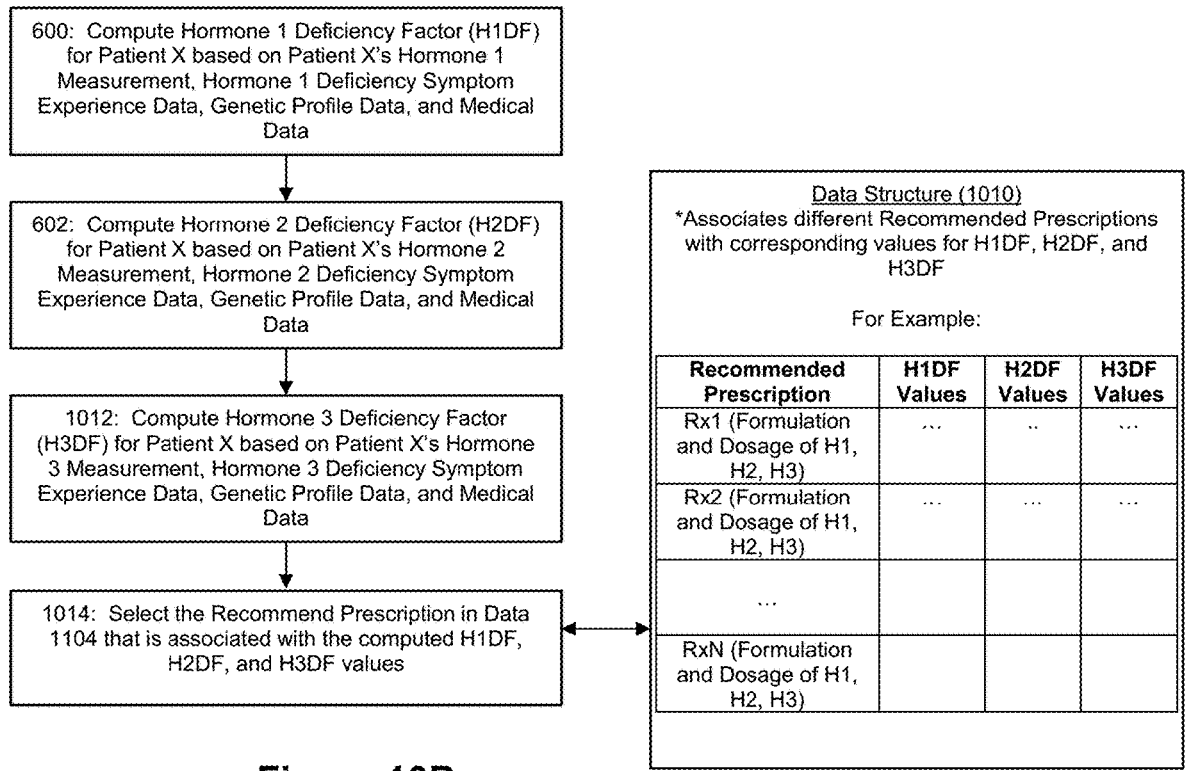
FIG. 10B depicts an example process flow for execution by a computer system to recommend hormone therapy treatment prescriptions of first, second, and third hormones.
FIG. 10C depicts an example of how third hormone deficiency factors can be systematically computed based on a person's biochemical and symptomatic status.

FIG. 10B shows an example process flow for the analysis program 1004. Steps 600 and 602 can operate as described above. At step 1012, the processor computes an H3 deficiency factor (H3DF) based on the subject patient's H3 measurement data 1000 and H3 deficiency symptom experience data (see 1002). The technique for computing H3DF can be similar to that described above for H1DF and H2DF. For example, H3DF can be computed as function of an H3 Measured Deficiency Factor and an H3 Deficiency Symptom Experience Factor. For example, H3DF can be computed as the product of the H3 Measured Deficiency Factor and the H3 Deficiency Symptom Experience Factor, as shown by FIG. 10C and discussed below.

In an example embodiment, the H3 Measured Deficiency Factor (H3MDF) can be computed according to an inverse relationship with the measured level of H3 for the subject patient from assay 210. Thus, in an example embodiment, H3MDF can be computed as:

$$H3MDF = \frac{1}{[H3M]} \quad \text{Equation (19)}$$

where H3M represents the measured level of H3 from assay 210. In an example where H3 is testosterone, the lowest possible score for H3DMF is expected to be $\frac{1}{25}=0.04$ (given that 25 ng/ml can be the treatment limit as noted above); and the highest possible store would be 1/1=1.

In an example embodiment, the H3 Deficiency Symptom Experience Factor (H3DSEF) can be computed as an aggregation of severity data experienced by the subject patient for different symptoms of an H3 deficiency. Thus, in an example embodiment, H3DSEF can be computed as:

$$H3DSEF = \Sum_{i=1}^{Q}(H3_S)_i \qquad \text{Equation (20)}$$

where Q represents the total number of different symptoms associated with an H3 deficiency, and where $(H1_S)_i$ represents the user-specified severity value for symptom i associated with an H3 deficiency. As noted above, in an example where H3 is testosterone, the system may be designed to take into consideration the 5 symptoms of testosterone deficiency as noted above. Thus, H3DSEF may range in value from 0 (no symptoms reported for all 5 symptoms) to 5 (maximum severity reported for all 5 symptoms). A practitioner may find it desirable to permit the H3DSEF value to zero out if no symptoms are present because there may not be a clinical need to treat women with testosterone if no testosterone deficiency symptoms are present (regardless of the measured testosterone level).

H3DF can then be computed from H3MDF and H3DSEF as follows:

$$H3DF = H3MDF \times H3DSEF \qquad \text{Equation (21)}$$

Returning to FIG. 10B, once the system has H1DF, H2DF, and H3DF values for the patient, the system can select a recommended prescription from data structure 1010. Data structure 1010 can operate in a fashion similar to data structure 410, but where data structure 1010 maps the various prescriptions to tuples of (H1DF, H2DF, H3DF). In examples where H3 is testosterone, it should be understood that some of the prescriptions within data structure 1010 may not include any testosterone (but may include different mixes of progesterone and estrogen).

Figure 10D:
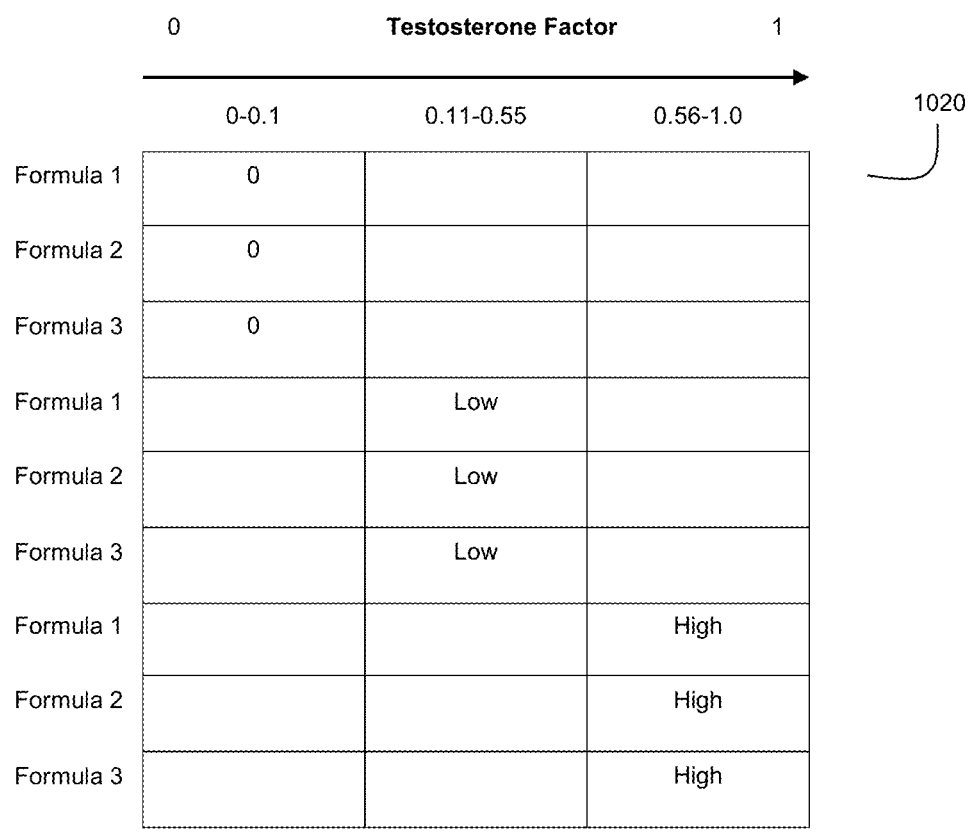

Furthermore, data structure 1010 may comprise multiple data structures. For example, a first data structure within data structure 1010 could be the data structure 410 that links H1DF and H2DF values to a particular formulation/dosage of H1 and H2, and a second data structure within data structure 1010 could be a data structure such as data structure 1020 shown by FIG. 10D that links formulations or prescriptions from data structure 410 with different testosterone dosages. In the example of FIG. 10D, where H1, H2, H3 are progesterone, estrogen, and testosterone, Formulations 1-3 can correspond to the different H1/H2 formulations from FIGS. 7E and 7F, and where different dosages of testosterone can be paired with each Formulation based on the H3DF score. In the example of FIG. 10D, this may be implemented as H3DF scores of 0.1 and below resulting in no testosterone treatment, H3DF scores between 0.11 and 0.55 resulting in a low dosage testosterone treatment, and H3DF scores between 0.56 and 1.0 resulting in a high dosage testosterone treatment. The system can establish appropriate amounts of testosterone to be used as low and high dosages. It should be understood that the testosterone factor ranges in FIG. 10D are examples; a practitioner may choose to modify such ranges as he or she deems appropriate.

FIG. 10E shows an example chart that illustrates how such an approach yields 9 unique prescriptions that can be recommended by the system. In this example, Formula 1 is progesterone-predominant (progesterone is provided in a higher clinical dose relative to estrogen) as noted above. Formula 2 provides doses of estrogen and progesterone in equal clinical strengths. Formula 3 is estrogen-predominant (estrogen is provided in a higher clinical concentration than progesterone). The table of FIG. 10E also shows relative concentrations of testosterone, which may take the form of DHEA, a preferred testosterone metabolite. Zero, low, or high clinical concentrations of testosterone are combined with Formulas 1-3 ultimately yielding 9 different formulations which can meet the clinical needs and provide appropriate treatment of the different stages and presentations of perimenopause menopause for more what is expected to be more than 95% of women when provided to them in various doses (how much of the product to use, described subsequently). It should be understood that FIG. 10E is merely an example; some practitioners may choose to employ a greater number of formulations, and or formulations with different mixes of clinical strengths for estrogen, progesterone, and testosterone.

It should also be understood that data structure 1010 could also be implemented as a single 3D data structure that maps the various prescriptions of H1-H3 in three dimensions, where the first, second, and third dimensions correspond to H1DF, H2DF, and H3DF respectively.

FIG. 10F shows an example GUI 1050 that can be used by mobile application 810 to collect symptom experience data from patients regarding testosterone deficiencies. Slider bars 1052 or other input mechanisms can be used with each symptom to permit the patient to quantity the severity of any experienced symptoms. Buttons such as buttons 1054, 1056, and 1058 can be provided to allow the user to, respectively, submit the entered-symptom experience data, clear the entered-symptom experience data, and navigate back to a previous screen.

Also, while the examples discussed above involve hormone therapy treatments with two or more hormones, it should also be understood that the technology described herein can be used to recommend or identify appropriate prescriptions of single hormones if appropriate for a given patient. With such an arrangement, the data structure 410 can reduce to a list of prescriptions indexed by a single hormone deficiency value (HDF). HDF can be computed in the same manner as discussed above for H1DF and H2DF. Thus, after the computer system 202 computes an HDF value for a patient based on the patient's biochemical, symptomatic, and genetic status, the computer system 202 can perform a lookup in the data structure 410 to find the prescription that is linked to the computed HDF value.

Further still, even in the case where the system considers treatment of the patient with a mix of two or more hormones (e.g., progesterone and estrogen), it may be the case that for some values of H1DF and H2DF, it is desirable to treat the patient with only one of the multiple hormones (rather than a mix of the two) (e.g., selecting only progesterone or estrogen for treatment). Accordingly, it should be understood that even with a grid data structure 410 as shown by FIGS. 7D and 7F, it may be the case that some of the cells 702 are populated with a prescription that treats the patient with only a single hormone. Thus, while an example embodiment is discussed above where the data structure 410 supports three different prescription formulations of progesterone and estrogen, a practitioner may choose to modify such a data structure to support 5 different prescription formulations of progesterone and estrogen (so that prescriptions of only estrogen and only progesterone are included). Similarly, while an example embodiment is discussed above where the data structure 410 supports 9 different prescription formulations of progesterone, estrogen, and testosterone, a practitioner may choose to modify such a data structure to support 11 different prescription formulations of progesterone, estrogen, and testosterone (so that prescriptions of only estrogen and only progesterone are included).

While the invention has been described above in relation to its example embodiments, various modifications may be made thereto that still fall within the invention's scope. Such modifications to the invention will be recognizable upon review of the teachings herein.

What is claimed is:

1. A system for providing hormone replacement therapy to a person, the system comprising:
    a biological sample assay configured to (1) analyze a bodily fluid sample from the person and (2) based on the analysis, (i) measure a level of a first hormone in the person, and (ii) measure a level of a second hormone in the person;
    a plurality of different formulations of the first and second hormones, biologically active forms thereof, analogs thereof, precursors thereof, and/or metabolites thereof;
    a user application for execution by a computer, the user application configured to (1) receive input that defines symptom experience data for the person with respect to a plurality of symptoms that relate to a plurality of conditions associated with deficiencies of the first and/or second hormones in a human;
    a memory configured to store (1) data representing the measured first hormone level from the biological sample assay, (2) data representing the second hormone level from the biological sample assay, (3) symptom experience data about the person received by the user application, (4) genetic profile data about the person, and (5) a data structure that associates a plurality of the different formulations with a first factor associated with the first hormone and a second factor associated with the second hormone; and
    a processor configured to (1) access the memory, (2) perform an analysis of the measured first hormone level data, the measured second hormone level data, the symptom experience data, and the genetic profile data, wherein the analysis translates the measured first hormone level data, the measured second hormone level data, the symptom experience data, and the genetic profile data into values for the first and second factors, (3) based on the analysis, generate a recommended hormone therapy prescription to treat a hormone deficiency condition experienced by the person, wherein the recommended hormone therapy prescription comprises (i) a selection from the data structure of the formulation associated with the translated first and second factor values and (ii) a dosage for the selection, (4) repeat its operations for a plurality of different persons over time such that the processor and memory (i) track the measured first and second hormone level data for the persons over time, (ii) track the symptom experience data for the persons over time, and (iii) track the recommended prescriptions for the persons over time, (5) adjust the analysis based on the tracked measured first and second hormone level data and the tracked symptom experience data for the persons over time in combination with the tracked recommend prescriptions for the persons over time, and adjust an assignment of prescriptions to first and second factors in the data structure based on the tracked measured first and second hormone level data and the tracked symptom experience data for the persons over time in combination with the tracked recommend prescriptions for the persons over time.

2. The system of claim 1 wherein the first hormone comprises progesterone, and wherein the second hormone comprises estrogen.

3. The system of claim 1 wherein the processor comprises a plurality of processors in a distributed computing system.

4. The system of claim 1 wherein the memory comprises a distributed memory.

5. A system for providing hormone replacement therapy to a person, the system comprising:
    a biological sample assay configured to (1) analyze a bodily fluid sample from the person and (2) based on the analysis, (i) measure a level of a first hormone in the person, and (ii) measure a level of a second hormone in the person;
    a plurality of different formulations of the first and second hormones, biologically active forms thereof, analogs thereof, precursors thereof, and/or metabolites thereof;
    a user application for execution by a computer, the user application configured to (1) receive input that defines symptom experience data for the person with respect to a plurality of symptoms that relate to a plurality of conditions associated with deficiencies of the first and/or second hormones in a human;
    a memory configured to store (1) data representing the measured first hormone level from the biological sample assay, (2) data representing the second hormone level from the biological sample assay, (3) symptom experience data about the person received by the user application, and (4) genetic profile data about the person;
    a processor configured to (1) access the memory, (2) perform an analysis of the measured first hormone level data, the measured second hormone level data, the symptom experience data, and the genetic profile data, wherein the analysis includes a computation of a measured deficiency value for the first hormone based on the measured first hormone level data such that the measured first hormone deficiency value has an inverse relationship with the measured first hormone level data, and (3) based on the analysis, generate a recommended hormone therapy prescription to treat a hormone deficiency condition experienced by the person, wherein the prescription comprises a selection of one of the different formulations and a dosage for the selection.

6. The system of claim 5 wherein the memory further comprises a data structure that associates a plurality of different prescriptions of the formulations with a first factor associated with the first hormone and a second factor associated with the second hormone; and
    wherein the analysis translates the measured first hormone level data, the measured second hormone level data, the symptom experience data, and the genetic profile data into values for the first and second factors; and
    wherein the processor is further configured to generate the recommended hormone therapy prescription based on a selection from the data structure of the prescription associated with the translated first and second factor values.

7. The system of claim 5 wherein the symptom experience data comprises first symptom experience data for symptoms experienced by the person that relate to conditions associated with deficiencies of the first hormone; and
    wherein the processor, as part of the analysis, is further configured to (1) compute a symptomatic deficiency value for the first hormone based on the first symptom experience data such that the symptomatic deficiency value exhibits larger values for relatively more severe symptoms for the conditions associated with deficiencies of the first hormone and smaller values for less severe symptoms for the conditions associated with deficiencies of the first hormone, and (2) compute a deficiency factor for the first hormone based on a combination of the computed first hormone measured deficiency value and the computed first hormone symptomatic deficiency value.

8. The system of claim 7 wherein the processor, as part of the analysis, is further configured to (1) compute a metabolism adjustment factor for the first hormone deficiency factor based on the genetic profile data for the person, and (2) adjust the first hormone deficiency factor based on the computed metabolism adjustment factor.

9. The system of claim 8 wherein the first hormone comprises progesterone, wherein the second hormone comprises estrogen, wherein the genetic profile data comprises a presence indicator for the person with respect to allelic status of one or more Cytochrome P450 (CP450) family genes, and wherein the processor is further configured to compute the metabolism adjustment factor for the first hormone deficiency factor such that the first hormone deficiency factor will be upwardly adjusted if the genetic profile data indicates the presence of an allele of a CP450 family of genes in the person linked to an increased rate of steroid metabolism in a human.

10. The system of claim 7 wherein the memory is further configured to store a body fat composition characteristic value for the person; and
wherein the processor, as part of the analysis, is further configured to (1) compute a body fat composition characteristic adjustment factor for the first hormone deficiency factor based on the body fat composition characteristic value for the person, and (2) adjust the first hormone deficiency factor based on the computed body fat composition characteristic adjustment factor.

11. The system of claim 7 wherein the processor, as part of the analysis, is further configured to (1) compute a risk adjustment factor for the first hormone deficiency factor based on the genetic profile data for the person, and (2) adjust the first hormone deficiency factor based on the computed risk adjustment factor.

12. The system of claim 11 wherein the first hormone comprises progesterone, wherein the second hormone comprises estrogen, wherein the genetic profile data comprises a presence indicator for the person with respect to allelic status of BRCA1 and BRCA2 genes, and wherein the processor is further configured to compute the risk adjustment factor for the first hormone deficiency factor such that the first hormone deficiency factor will be zero if the genetic profile data indicates the presence of either the BRCA1 or BRCA2 gene alleles in the person linked to an increased risk of breast cancer associated with hormone replacement therapy.

13. The system of claim 5 wherein the first hormone comprises progesterone, and wherein the second hormone comprises estrogen.

14. The system of claim 5 wherein the processor comprises a plurality of processors in a distributed computing system.

15. The system of claim 5 wherein the memory comprises a distributed memory.

16. A system for providing hormone replacement therapy to a person, the system comprising:
a biological sample assay configured to (1) analyze a bodily fluid sample from the person and (2) based on the analysis, (i) measure a level of a first hormone in the person, and (ii) measure a level of a second hormone in the person;
a plurality of different formulations of the first and second hormones, biologically active forms thereof, analogs thereof, precursors thereof, and/or metabolites thereof;
a user application for execution by a computer, the user application configured to (1) receive input that defines symptom experience data for the person with respect to a plurality of symptoms that relate to a plurality of conditions associated with deficiencies of the first and/or second hormones in a human;
a memory configured to store (1) data representing the measured first hormone level from the biological sample assay, (2) data representing the second hormone level from the biological sample assay, (3) symptom experience data about the person received by the user application, (4) genetic profile data about the person, and (5) a data structure that associates a plurality of the different formulations with different values for the first and second hormone deficiency factors; and
a processor configured to (1) access the memory, (2) perform an analysis of the measured first hormone level data, the measured second hormone level data, the symptom experience data, and the genetic profile data, wherein the analysis includes (i) a computation of a value for a first hormone deficiency factor based on the measured first hormone level data and the symptom experience data and (ii) a computation of a value for a second hormone deficiency factor based on the measured second hormone level data and the symptom experience data, and (3) based on the analysis, generate a recommended hormone therapy prescription to treat a hormone deficiency condition experienced by the person, wherein the recommended hormone therapy prescription comprises (i) a selection from the data structure of the formulation associated with the computed first and second hormone deficiency factor values and (ii) a dosage for the selection.

17. The system of claim 16 wherein the data structure represents a grid of cells, each cell corresponding to different prescriptions of the first and second hormones and being indexed in a coordinate space by a pair of values for the first and second hormone deficiency factors, wherein the grid has a first axis and a second axis that define the coordinate space, wherein the first axis has a range of values for the first hormone deficiency factor, and wherein the second axis has a range of values for the second hormone deficiency factor.

18. The system of claim 17 wherein the different prescriptions are a set of X different prescriptions, and wherein the data structure associates the different members of the X prescriptions with the cells that are deemed clinically appropriate for the person based on the cell's associated first and second hormone deficiency factor values.

19. The system of claim 18 wherein the first hormone comprises progesterone, wherein the second hormone comprises estrogen, and wherein X is a value between 3 and 5.

20. The system of claim 18 wherein prescriptions with a higher dose of the first hormone, biologically active form thereof, analog thereof, precursor thereof, and/or metabolite thereof relative to the second hormone, biologically active form thereof, analog thereof, precursor thereof, and/or metabolite thereof in the formulation are associated with cells of the grid that are associated with first hormone deficiency factor values above a first threshold and second hormone deficiency factor values below a second threshold;

wherein prescriptions with a higher dose of the second hormone, biologically active form thereof, analog thereof, precursor thereof, and/or metabolite thereof relative to the first hormone, biologically active form thereof, analog thereof, precursor thereof, and/or metabolite thereof in the formulation are associated with cells of the grid that are associated with second hormone deficiency factor values above a third threshold and first hormone deficiency factor values below a fourth threshold; and wherein prescriptions with doses of the first and second hormone, biologically active forms thereof, analogs thereof, precursors thereof, and/or metabolites thereof that are of relatively equal clinical strengths in the formulation are associated with cells of the grid that are associated with first hormone deficiency factor values between the first and fourth thresholds and second hormone deficiency factor values between the second and third thresholds.

21. The system of claim 18 wherein the recommended prescription further comprises a third hormone, wherein the first hormone comprises progesterone, wherein the second hormone comprises estrogen, wherein the third hormone comprises testosterone, and wherein X is a value between 9 and 11.

22. The system of claim 16 wherein the first hormone comprises progesterone, and wherein the second hormone comprises estrogen.

23. The system of claim 16 wherein the processor comprises a plurality of processors in a distributed computing system.

24. The system of claim 16 wherein the memory comprises a distributed memory.

25. A system for providing hormone replacement therapy to a person, the system comprising:
- a biological sample assay configured to (1) analyze a bodily fluid sample from the person and (2) based on the analysis, (i) measure a level of a first hormone in the person, and (ii) measure a level of a second hormone in the person;
- a plurality of different formulations of the first and second hormones, biologically active forms thereof, analogs thereof, precursors thereof, and/or metabolites thereof;
- a user application for execution by a computer, the user application configured to (1) receive input that defines symptom experience data for the person with respect to a plurality of symptoms that relate to a plurality of conditions associated with deficiencies of the first and/or second hormones in a human;
- a memory configured to store (1) data representing the measured first hormone level from the biological sample assay, (2) data representing the second hormone level from the biological sample assay, (3) symptom experience data about the person received by the user application, (4) genetic profile data about the person, and (5) a data structure that associates a plurality of the different formulations with a first factor associated with the first hormone and a second factor associated with the second hormone;
- a processor configured to (1) access the memory, (2) perform an analysis of the measured first hormone level data, the measured second hormone level data, the symptom experience data, and the genetic profile data, wherein the analysis translates the measured first hormone level data, the measured second hormone level data, the symptom experience data, and the genetic profile data into values for the first and second factors, and (3) based on the analysis, generate a recommended hormone therapy prescription to treat a hormone deficiency condition experienced by the person, wherein the recommended hormone therapy prescription comprises (i) a selection from the data structure of the formulation associated with the translated first and second factor values and (ii) a dosage for the selection.

26. The system of claim 25 wherein the user application is further configured to provide a user interface for display on a display screen, the user interface configured to receive input that defines the symptom experience data.

27. The system of claim 26 wherein the user interface includes a plurality of slider bars, each slider bar corresponding to a different symptom relating to a condition associated with a deficiency of the first and/or second hormone, and wherein the slider bar is adjustable in response to input to define a value within a range of values for severity of its corresponding symptom, and wherein the symptom experience data comprises the input-defined severity values.

28. The system of claim 25 wherein the processor is resident in a server, and wherein the user application comprises a mobile application configured for execution by a mobile computing device.

29. The system of claim 25 wherein the memory is further configured to store medical information about the person, and wherein the analysis is also performed on the medical information, wherein the medical information comprises a body fat composition characteristic for the person and/or a surgical history for the person.

30. The system of claim 25 wherein the genetic profile data comprises gene data about whether the person has an allele of a gene which affects a person's metabolism of the first and/or second hormones.

31. The system of claim 25 wherein the genetic profile data comprises gene data about whether the person has an allele of a gene linked to an adverse health risk for a human if the human is treated with the first and/or second hormones.

32. The system of claim 25 further comprising:
- a plurality of different formulations of a third hormone, biologically active forms thereof, analogs thereof, precursors thereof, and/or metabolites thereof;
- wherein the memory is further configured to store (1) data representative of a measured level of the third hormone in the person, and (2) symptom experience data for a plurality of symptoms experienced by the person that relate to a plurality of conditions associated with a deficiency of the third hormone;
- wherein the analysis includes an analysis of the measured first hormone level data, the measured second hormone level data, the measured third hormone level data, the symptom experience data for symptoms experienced by the person that relate to conditions associated with deficiencies of the first, second, and third hormones, and the genetic profile data; and
- wherein the recommended hormone therapy prescription further comprises a selection of one of the third hormone formulations and a dosage for the third hormone formulation.

33. The system of claim 25 wherein the processor is further configured to repeat its operations for the person over time;
- wherein the processor and memory are further configured to (1) track the measured first and second hormone level data for the person over time, and (2) track the symptom experience data for the person over time; and wherein the processor is further configured to adjust the analysis based on the tracked measured first and second hormone level data and the tracked symptom experience data.

34. The system of claim 25 wherein the processor is further configured to repeat its operations for a plurality of different persons over time such that the processor and memory (1) track the measured first and second hormone level data for the persons over time, (2) track the symptom experience data for the persons over time, and (3) track the recommended prescriptions for the persons over time;
wherein the processor is further configured to adjust the analysis based on the tracked measured first and second hormone level data and the tracked symptom experience data for the persons over time in combination with the tracked recommend prescriptions for the persons over time.

35. The system of claim 25 wherein the first hormone comprises progesterone, and wherein the second hormone comprises estrogen.

36. The system of claim 25 wherein the person puts the system to use to treat the hormone deficiency condition with the formulation selection in accordance with the recommended hormone therapy prescription.

37. The system of claim 25 wherein a medical professional puts the system to use to provide the recommended hormone therapy prescription to the person.

38. The system of claim 25 wherein a pharmacy puts the system to use to sell the formulation selection to the person.

39. The system of claim 25 further comprising:
a plurality of biological sample assays for a plurality of persons, each biological sample assay configured to (1) analyze a bodily fluid sample from a different person and (2) based on the analysis, (i) measure a level of a first hormone in that person, and (ii) measure a level of a second hormone in that person; and
a plurality of user applications for execution by a plurality of computers, each user application associated configured to (1) receive input that defines symptom experience data for at least one of the persons with respect to a plurality of symptoms that relate to a plurality of conditions associated with deficiencies of the first and/or second hormones in a human;
wherein the memory is further configured to store, for each of a plurality of persons, (1) data representing the measured first hormone level from the biological sample assay for that person, (2) data representing the second hormone level from the biological sample assay for that person, (3) symptom experience data about the persons received by the user applications, and (4) genetic profile data about the persons; and
wherein the processor is further configured to perform the analysis and the generation of the recommended hormone therapy prescription for each of a plurality of the persons.

40. The system of claim 39 wherein the user applications are configured to receive the symptom experience data from the persons over time;
wherein the processor is further configured to update the memory over time to track efficacy data for the prescriptions over time with respect to the recommended prescriptions.

41. The system of claim 40 wherein a party that maintains the memory and the processor puts the system to use to analyze the efficacy data in the memory and adjust the analysis based the analysis of the efficacy data.

42. The system of claim 25 further comprising a second biological sample assay configured to (1) analyze a nucleic acid sample from the person and (2) based on the analysis, provide the person's genetic profile.

43. The system of claim 25 wherein the processor comprises a plurality of processors in a distributed computing system.

44. The system of claim 25 wherein the memory comprises a distributed memory.

45. A method for hormone therapy treatment of a person based on a systematic analysis of a person's biochemical, symptomatic, and genetic status, the method comprising:
determining a deficiency factor value for a first hormone based on an analysis of (1) a measured level of the first hormone in the person, (2) symptom experience data for the person with respect to a plurality of symptoms that relate to a plurality of conditions associated with a deficiency of the first hormone in a human, and (3) genetic profile data for the person;
determining a deficiency factor value for a second hormone based on an analysis of (1) a measured level of the second hormone in the person, (2) symptom experience data for the person with respect to a plurality of symptoms that relate to a plurality of conditions associated with a deficiency of the second hormone in a human, and (3) genetic profile data for the person;
selecting an effective formulation and dose of the first and second hormones, biologically active forms thereof, analogs thereof, precursors thereof, and/or a metabolites thereof for treating the person based on the determined first and second hormone deficiency factor values; and
administering to the person the selected effective formulation and dose.

46. The method of claim 45 wherein the first hormone comprises progesterone, and wherein the second hormone comprises estrogen.

* * * * *